(12) United States Patent  (10) Patent No.: US 8,688,225 B2
Panken et al.  (45) Date of Patent: Apr. 1, 2014

(54) POSTURE STATE DETECTION USING SELECTABLE SYSTEM CONTROL PARAMETERS

(75) Inventors: Eric J. Panken, Edina, MN (US); Dennis M. Skelton, Minneapolis, MN (US)

(73) Assignee: Medtronic, Inc., Minneapolis ( * ) Notice: Subject to any disclaimer, the term of this patent is extended or adjusted under 35 U.S.C. 154(b) by 1158 days.

(21) Appl. No.: 12/433,029

(22) Filed: Apr. 30, 2009

(65) Prior Publication Data

US 2010/0010384 A1 Jan. 14, 2010

Related U.S. Application Data

(60) Provisional application No. 61/080,049, filed on Jul. 11, 2008.

(51) Int. Cl.
*A61N 1/00* (2006.01)
(52) U.S. Cl.
USPC .................................................. 607/62
(58) Field of Classification Search
USPC .................... 607/62, 17–19, 30, 59
See application file for complete search history.

(56) References Cited

U.S. PATENT DOCUMENTS

| | | | |
|---|---|---|---|
| 4,297,685 A | 10/1981 | Brainard, II | |
| 4,365,633 A | 12/1982 | Loughman | |
| 4,543,955 A | 10/1985 | Schroeppel | |
| 4,550,736 A | 11/1985 | Broughton et al. | |
| 4,566,456 A | 1/1986 | Koning et al. | |
| 4,771,780 A | 9/1988 | Sholder | |
| 4,776,345 A | 10/1988 | Cohen et al. | |
| 4,846,180 A | 7/1989 | Buffet | |
| 4,846,195 A | 7/1989 | Alt | |
| 5,031,618 A | 7/1991 | Mullett | |

(Continued)

FOREIGN PATENT DOCUMENTS

| | | |
|---|---|---|
| DE | 19831109 | 1/2000 |
| DE | 10024103 | 11/2001 |

(Continued)

OTHER PUBLICATIONS

"Analysis of heart rate dynamics by methods derived from non-linear mathematics: Clinical applicability and prognostic significance," http://herkules.oulu.fi.isbn9514250133/html, 4 pp., 2004.

(Continued)

*Primary Examiner* — Christopher D Koharski
*Assistant Examiner* — Nadia Ahmad
(74) *Attorney, Agent, or Firm* — Beth L. McMahon

(57) ABSTRACT

Techniques for detecting and classifying a posture state of a patient are disclosed, wherein a posture state includes at least one of a posture and/or an activity state related to motion. In one embodiment, one or more signals indicative of at least one of posture and activity state of the patient may be sensed by a sensor. Control logic may be provided to process the one or more sensed signals in a selectable manner. This selectable manner may be based on current posture state data describing a posture state in which the patient has previously been classified. Alternatively or additionally, this current posture state data may describe a posture state transition previously undergone by the patient. The one or more signals that are so processed may then be used to classify a posture state of the patient.

44 Claims, 10 Drawing Sheets

(56) References Cited

U.S. PATENT DOCUMENTS

| | | |
|---|---|---|
| 5,040,534 A | 8/1991 | Mann et al. |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,038,475 A | 3/2000 | Sikorski et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,879,352 B1 | 4/2005 | Kim |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 * | 12/2006 | Koh et al. .................. 607/60 |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |

(56) References Cited

U.S. PATENT DOCUMENTS

| | | |
|---|---|---|
| 7,210,240 B2 | 5/2007 | Townsend et al. |
| 7,212,862 B2 | 5/2007 | Park et al |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Heruth et al. |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0113710 A1 | 5/2005 | Stahmann et al. |
| 2005/0113887 A1 | 5/2005 | Bauhahn |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 | 11/2005 | Miesel |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0284979 A1 | 12/2006 | Clarkson |
| 2006/0287686 A1 | 12/2006 | Cullen et al. |
| 2007/0015976 A1 | 1/2007 | Miesel et al. |
| 2007/0032748 A1 | 2/2007 | McNeill et al. |
| 2007/0038265 A1 | 2/2007 | Tcheng et al. |
| 2007/0050715 A1 | 3/2007 | Behar |
| 2007/0073355 A1 | 3/2007 | DiLorenzo et al. |
| 2007/0115277 A1 | 5/2007 | Wang et al. |
| 2007/0118056 A1 | 5/2007 | Wang et al. |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 | 6/2007 | Bourget et al. |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |

(56) References Cited

U.S. PATENT DOCUMENTS

| | | |
|---|---|---|
| 2008/0081958 A1 | 4/2008 | Denison et al. |
| 2008/0114219 A1 | 5/2008 | Zhang et al. |
| 2008/0164979 A1 | 7/2008 | Otto |
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 | 10/2008 | Gerber et al. |
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | James et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0106210 A1 | 4/2010 | Hedberg et al. |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1731097 A2 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

"Design Competition: Runners-Up for the Best Three Designs," EPN, vol. 26, No. 1, 1 pg., 2002.

"IBM and Citizen Watch develop Linux-Based WatchPad," http://wwwlinuxdevices.com/news/NS6580187845.html, 5 pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308, 1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

Ang et al., "Physical model of a MEMS accelerometer for low-g motion tracking applications," 2004 IEEE International Conference on Robotics and Automation, vol. 2, pp. 1345-1351, 2004.

Buchser et al., "Improved Physical Activity in Patients Treated for Chronic Pain by Spinal Cord Stimulation," Neuromodulation, vol. 8, Issue 1, pp. 40-48, Mar. 2005.

Crago et al., "An Elbow Extension Neuroprosthesis for Individuals with Tetraplegia," IEEE Transactions on Rehabilitation Engineering, vol. 6, No. 1, pp. 1-6, Mar. 1998.

Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.

Dinner, "Effect of Sleep on Epilepsy," Journal of Clinical Neurophysiology, American Clinical Neurophysiology Society, 19(6), pp. 504-513, 2002.

Foerster et al., "Motion Pattern and Posture: Correctly Assessed by Calibrated Accelerometers," Forschungsgrupe Psychophysiologie, Universität Freiburg, Germany, Mar. 2000, 28 pp.

(56) References Cited

OTHER PUBLICATIONS

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.
Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.
Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.
Goodrich et al., "The Prediction of Pain Using Measures of Sleep Quality," Pain Digest, 8:23-25, 1998.
Heinz et al., "Using Wearable Sensors for Real-time Recognition Tasks in Games of Martial Arts—An Initial Experiment," Institute for Computer Systems and Networks (CSN), UMIT-University of Health Systems, Medical Informatics and Technology Hall in Tyrol, Austria, 2006 5 pp. http://eis.comp.lancs.ac.uk/fileadmin/relate/publication/2006-WearableSensors.pdf.
Hendelman et al., "Validity of Accelerometry for the Assessment of Moderate Intensity Physical Activity in the Field," Medicine & Science in Sports & Exercise, pp. S442-S449, 2000.
Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.
Husak, "Model of Tilt Sensor Systems, "ICECS 2002, $9^{th}$ IEEE International Conference on Electronics, Circuits and Systems, vol. 1, pp. 227-230, 2002.
Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.
Kassam, "2005 EDP Topic "MK4": Tremor Data-Logger for Parkinson's Disease Patients," http://www.ee.ryerson.ca/~courses/edp2005/MK4.html, 3 pp., 2005.
Kerr et al., "Analysis of the sit-stand-sit movement cycle in normal subjects," Clinical Biomechanics, vol. 12, No. 4, pp. 236-245, 1977.
Kiani et al., "Computerized Analysis of Daily Life Motor Activity for Ambulatory Monitoring," Technology and Health Care 5, pp. 307-318, 1997.
Kitchin et al., "Compensating for the 0 g Offset Drift of the ADXL50 Accelerometer," Analog Devices Application Note AN-380, 2 pp.
Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.
Leiper et al., "Sensory Feedback for Head Control in Cerebral Palsy," Physical Therapy, vol. 61, No. 4, pp. 512-518, Apr. 1981.
Lorussi, "Wearable, Redundant Fabric-Based Sensor Arrays for Reconstruction of Body Segment Posture," IEEE Sensors Journal, vol. 4, No. 6, pp. 808-817, Dec. 2004.
Mathie et al., "A Pilot Study of Long-Term Monitoring of Human Movements in the Home Using Accelerometer," Journal of Telemedicine and Telecare10:144-151, Jun. 2007.
Mathie et al., "Determining Activity Using a Triaxial Accelerometer," Proceedings of the Second Joint EMBS/BMES Conference, Houston, TX, pp. 2481-2482, Oct. 23-26, 2002.
Mattmann et al., "Recognizing Upper Body Postures Using Textile Strain Sensors," Proceedings Eleventh IEEE International Symposium on Wearable Computers, ISWC, pp. 29-36, 2007.
Mendez et al., "Interactions Between Sleep and Epilepsy," Journal of Clinical Neurophysiology, American Clinical Neurophysiology Society, 18(2), pp. 106-127, 2001.
Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.

Slyper et al., "Action Capture with Accelerometers," Eurographics/ACM SIGGRAPH Symposium on Computer Animation, Carnegie Mellon University, 7 pp. 2008.
Smith et al., "How do sleep disturbance and chronic pain inter-relate? Insights from the longitudinal and cognitive-behavioral clinical trials literature," Sleep Medicine Reviews, YSMRV 286, pp. 1-14, 2003.
Smith et al., "Presleep cognitions in Patients with Insomnia Secondary to Chronic Pain," Journal of Behavioral Medicine, vol. 24, No. 1, pp. 93-114, 2001.
Emmanuel Munguia Tapia,"Activity Recognition from Accelerometer Data for Videogame Applications," http://alumni.media.mit.edu/~emunguia/html/videogames.htm, 7 pp., Dec. 2, 2003, printed Oct. 1, 2009.
Trolier-Mckinstry et al., "Thin Film Piezoelectrics for MEMS," Journal of Electroceramics, v. 12, No. 1-2, pp. 7-17, Jan./Mar. 2004.
Tuck, "Implementing Auto-Zero Calibration Technique for Accelerometers," Freescale Semiconductor Application Note AN3447, 5 pp., Mar. 2007.
Tuisku, "Motor Activity Measured by Actometry in Neuropsychiatric Disorders," Department of Psychiatry, University of Helsinki, Helsinki, Finland, 115 pp., 2002.
Vega-Gonzalez, "Upper Limb Activity Monitoring," Arch Phys Med Rehabil, vol. 86, pp. 541-548, Mar. 2005.
Velten et al., "A New Three-Axis Accelerometer," Sensor '99—$9^{th}$ Int'l Traide Fair and Conference for Sensors/Transducers & Systems, Nürnberg, Germany, May 18-20, 1999, Sensor '99 Proceedings II, A 5.2, pp. 47-52, 1999.
PCT/US09/48676: International Search Report and Written Opinion dated Apr. 7, 2010, 16 pp.
U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/771,854, filed Apr. 30, 2010, Skelton.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.

* cited by examiner

POSTURE STATE DETECTION USING SELECTABLE SYSTEM CONTROL PARAMETERS

RELATED APPLICATIONS

The following application claims priority to provisionally-filed U.S. Patent Application entitled "Posture State Detection System and Method", Patent Application Ser. No. 61/080,049, filed Jul. 11, 2008, which is incorporated herein by reference in its entirety.

The following applications include some subject matter related to, or in common with, the following, and are incorporated herein by reference in their entireties:

"Posture State Classification for a Medical Device" Ser. No. 12/433,004 filed on even date herewith;

"Posture State Classification for a Medical Device" Ser. No. 12/432,993 filed on even date herewith;

"Posture State Responsive Therapy Delivery using Dwell Times", Ser. No. 12/433,017, filed on even date herewith; and "Reorientation of Patient Posture States for Posture-Responsive Therapy", Ser. No. 12/433,623 filed on even date herewith.

TECHNICAL FIELD

The invention relates to posture detection techniques, and more particularly, to medical devices that detect posture states.

BACKGROUND OF THE INVENTION

A variety of types of medical devices are used for chronic, e.g., long-term, provision of therapy to patients. As examples, pulse generators are used for provision of cardiac pacing and neurostimulation therapies and pumps are used for delivery of therapeutic agents, such as drugs. Typically, such devices provide therapy continuously or periodically according to parameters. For instance, a program comprising respective values for each of a plurality of parameters may be specified by a clinician and used to deliver the therapy.

It may be desirable in some circumstances to activate and/or modify the therapy based on a patient state. For example, the symptoms such as the intensity of pain of patients who receive spinal cord stimulation (SCS) therapy may vary over time based on the activity level or posture of the patient, the specific activity undertaken by the patient, or the like. It is desirable to be able to detect and classify the state of the patient accurately so that this classification may be used to activate and/or select a therapy that is most efficacious for that state.

SUMMARY OF THE INVENTION

In general, the invention is directed to techniques for detecting and classifying a posture state of a patient, which may include classifying a patient posture and/or a patient activity state. The detection of a posture state may then be used to prompt some action on behalf of the user. Such action may involve automatically delivering therapy to a patient according to therapy information previously associated with the detected posture state. Other actions may involve triggering the recording of physiological data when the patient is detected as being in a certain posture state. Still other actions may relate to providing a notification, such as may be required if the posture state indicates the patient may have taken a fall.

In one embodiment, classification of a patient's posture may be performed by comparing sensor signals (e.g., a detected vector) indicative of the patient's posture with one or more other signal levels that are associated with previously defined postures. Based on this comparison, a patient may be classified as being in a posture described by one of the posture definitions. If this comparison indicates that the detected parameters have a predetermined relationship to parameters associated with one of the defined postures, the patient's posture is classified according to that defined posture. Some type of action may then be taken in response to this classification. For instance, therapy delivery may be initiated, or currently-delivered therapy may be modified.

Similarly, classifying a patient's activity state may involve determining a level of motion, a vector describing motion (e.g., describing direction of velocity or acceleration), or some other descriptor indicative of activity. To classify a patient's activity state, signals obtained from a sensor that describe a patient's activity may be compared to signal values associated with activity state definitions. Based on this comparison, the patient may be classified as being in one of the activity states described by one of the definitions. In response, some type of action may be initiated. For example, some type of therapy may be initiated, or therapy parameters may be modified.

Posture definitions and activity state definitions may each be described as being a subset of a more general posture state definition. A posture state definition may specify a posture, an activity state, or both. According to a general approach, signals describing either a patient's posture, activity state, or both, may be compared to signal values included in posture state definitions. The patient's posture state may be classified based on this comparison so that therapy may be delivered to a patient according to therapy parameter values associated with the classified posture state definition. Alternatively, or additionally, some other type of action may be taken in response to this classification, such as providing a notification, initiating recording of data, initiating a communication session with an external device, and so on.

As a patient's posture state is classified, information describing this state may be recorded as information referred to as current posture state data. For example, the current posture state data may identify the posture state in which the patient was most recently classified. Alternatively or additionally, the current posture state data may identify a posture state transition that was recently experienced by the patient. This information may be used to control various control aspects of the system, as is discussed below.

In one embodiment, signals from the sensor may be processed before they are used to classify a patient's posture and/or activity state. Such processing may, for instance, extract a DC signal portion for use in classifying a patient's posture. Similarly, an AC signal portion may be used to classify a patient's activity state. Processing may involve signal sampling, filtering to remove noise, and other signal processing techniques that may be employed to more optimally obtain signals that can be used to classify a patient's posture state.

In some embodiments of the invention, system control parameters are employed to obtain and to process signals from the sensor. These system control parameters may be programmable. In one embodiment, these system control parameters may be selected based on the current posture state data. For instance, system control parameters used to obtain and process sensor signals may be selected based on the patient's current posture, the patient's current activity level, or both. System control parameters may alternatively or additionally be selected based on a patient transitioning between two specific postures, activity levels, or both. This will allow signal capture and processing to be carried out in a manner tailored to current conditions.

According to one aspect of this disclosure, a medical device system is described that includes a storage device to store current posture state data describing a posture state in which a patient has previously been classified. A sensor to sense one or more signals indicative of at least one of a posture and an activity state of the patient is also disclosed. Control logic is provided to process the one or more signals in a selectable manner that is based on the current posture state data, and to classify a patient as being in a posture state indicated by the processed one or more signals.

Another aspect relates to a method comprising receiving a signal from a sensor that indicates a posture state of a patient, and obtaining current posture state data identifying a posture state in which the patient was most recently classified. The received signals are processed in a manner that is based on the current posture state data to determine at least one of an activity state and a posture of the patient, and a response is initiated based on the classification of the processed signals.

Another method according to the disclosure relates to receiving a signal from a sensor that indicates a posture state of a patient. Current posture state data identifying a posture state in which the patient was most recently classified is obtained from a storage device. The received signal is processed based on the current posture state data to determine an activity state of the patient. The current posture state data is updated based on the determined activity state of the patient.

Another embodiment relates to a digital storage medium for storing instructions executed to cause a processor to perform a method. The method includes receiving signals indicating a posture of a patient, retrieving current posture state data indicating a posture state in which the patient was classified, processing the received signals in a manner controlled by the current posture state data, and determining from the processed signals a classification of the posture of the patient.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

Figure 1:
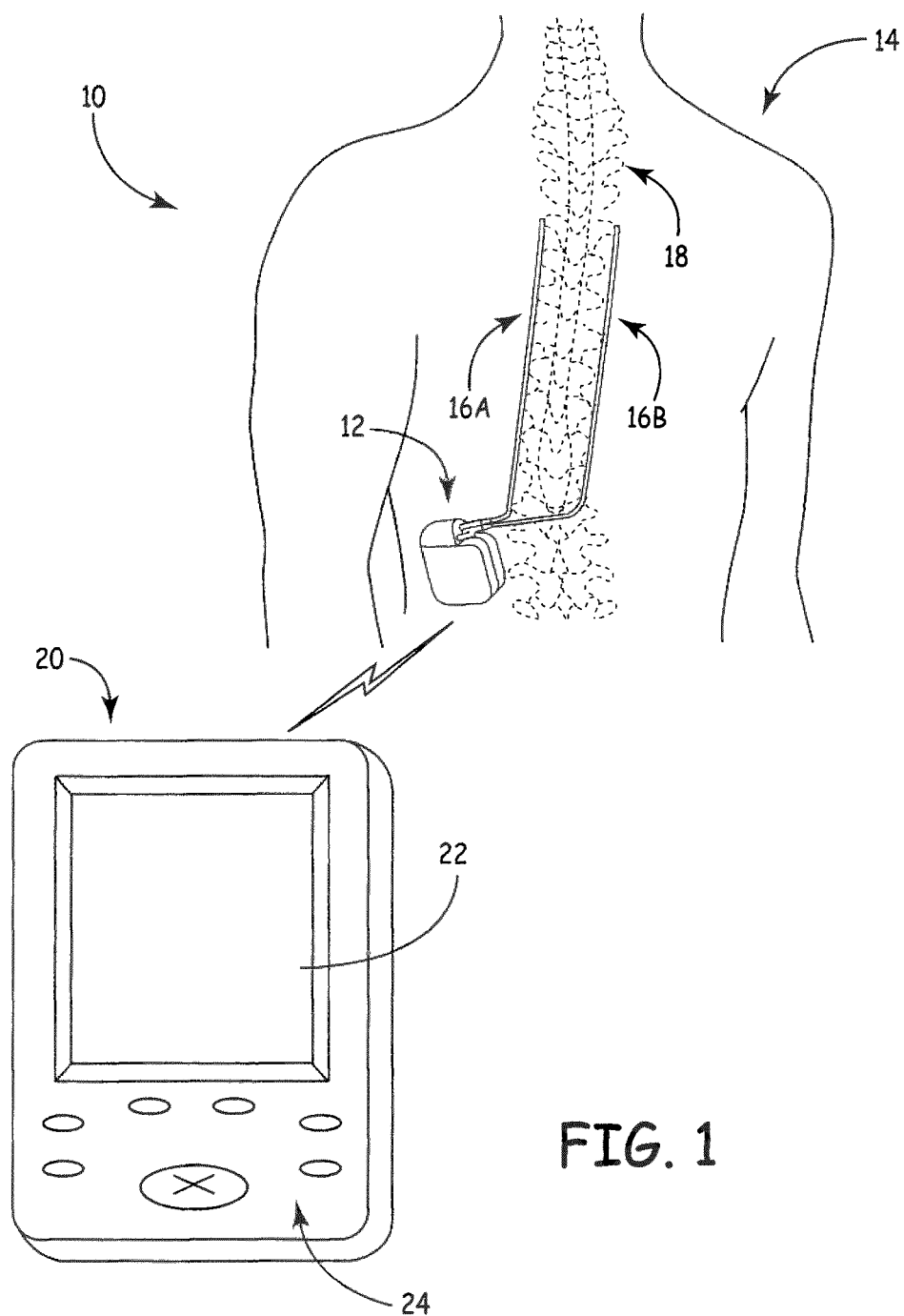
FIG. 1 is a conceptual diagram illustrating an example system that facilitates the definition and classification of posture states according to the disclosure.

Techniques described herein relate to using one or more signals from a sensor to classify a patient's posture. As used herein, "signal" refers to a logical signal, as may be described by logic levels transmitted on one or more physical connections of an interface in parallel or in series. For instance, a signal may be described by voltage levels transmitted in parallel on a multi-line interface, or in series on a single-line interface.

According to the disclosure, posture classification may, in one embodiment, be performed by first creating posture definitions that describe postures a patient may assume. Once such definitions are created, signals obtained from a sensor that describe the patient's current posture may be compared with one or more other signal levels that have been associated with the defined postures. If this comparison indicates that the signals obtained from the sensor have a predetermined relationship to signal values associated with a defined posture, the patient's posture is classified according to that defined posture. Some action may then be initiated in response to this posture classification. For instance, therapy may then be delivered to the patient using therapy parameters that have previously been associated with the posture in which the patient is currently classified. Alternatively or additionally, some other action may be taken, such as providing a notification (e.g., indicating a potential fall), initiating the storing of data, and so on.

In a similar manner, aspects of the current disclosure relate to classifying a patient's activity state, and then delivering therapy or performing some other action based on that classification. A patient's activity state relates to the motion or activity of the patient. The activity state may describe, for example, an overall activity level (e.g., footfalls), an activity level in one or more selected directions, a vector associated with velocity or acceleration of motion, and so on. To classify a patient's activity state, signals indicative of that activity state may be compared to signal values associated with activity state definitions. Based on this comparison, therapy parameters may be selected for use in delivering therapy to a patient.

Posture definitions and activity state definitions may each be described as being a subset of a more general posture state definition. A posture state definition may specify a posture, an activity state, or both. According to a general approach, signals describing either a patient's posture, activity state, or both, may be compared to signal values included in posture state definitions. The patient's posture state may be classified based on this comparison so that therapy may be delivered to a patient according to therapy parameter values associated with the classified posture state definition. Alternatively, or additionally, some other type of action may be taken in response to this classification, such as providing a notification, initiating recording of data, initiating a communication session with an external device, and so on.

Examples of therapies that may be delivered in a closed-loop manner according to the present disclosure include electrical stimulation or the delivery of therapeutic agents. Electrical stimulation may be used, for example, to treat patients that suffer from chronic back pain, leg pain, or other pain that cannot be treated through other methods. As a patient changes posture state, which may involve changes in position and/or activity level, the stimulation may need to be adjusted in order to maintain efficacy. Such changes in a patient's posture state may be detected, classified, and used to modify a therapy that is currently being delivered, or select a new therapy for delivery to the patient. Other types of therapies, such as drug delivery therapy, may be modified in a similar manner in response to detected posture state transitions. In another embodiment, the detected posture state transitions may be used to prompt some notification, or to record some information.

According to some embodiments of the disclosure, a patient's posture state is sensed using signals obtained from a sensor. This sensor may be housed within an implantable medical device (IMD), or may be communicatively or otherwise coupled to the IMD. The sensor may be a three-axis accelerometer such as a piezoelectric and/or micro-electromechanical (MEMs) accelerometer. The sensed signals may be used to classify a posture state that is then employed to determine a therapy adjustment.

Posture state classification may be performed using a data structure that associates signal values obtained from a sensor (e.g. accelerometer) with posture states. This association may be used to classify a patient's posture state. This classification may then be used to select an appropriate therapy, as may be accomplished using the same, or another data structure. Therapy parameters may be selected that provide the most efficacious results based on the patient's current posture state.

In one embodiment, signals from the sensor may be processed before they are used to classify a patient's posture state. Such processing may, for instance, extract a DC signal portion for use in classifying a patient's posture. Similarly, an AC signal portion may be used to classify a patient's activity state. Processing may involve signal sampling, filtering to remove noise, and other signal processing techniques that may be employed to more optimally obtain signals that can be used to classify a patient's posture state.

In some embodiments of the invention, system control parameters are employed to obtain and to process signals from the sensor. These system control parameters may be programmable. In one embodiment, these system control parameters may be selected based on a patient's current posture state, or on a posture state transition recently undergone by the patient. For instance, system control parameters used to obtain and process sensor signals may be selected based on the patient's current posture, the patient's current activity level, or both. System control parameters may alternatively or additionally be selected based on a patient transitioning between two specific postures, activity levels, or both. This will allow signal capture and processing to be carried out in a manner tailored to current conditions.

FIG. 1 is a conceptual diagram illustrating an example system 10 that facilitates the definition and classification of posture states according to the invention. These posture states may then be utilized to deliver therapy to a patient. In the illustrated example, system 10 includes an IMD 12, which is implanted within a patient 14, and delivers neurostimulation therapy to patient 14.

IMD 12 delivers neurostimulation therapy to patient 14 via therapy connections 16A and 16B (collectively "therapy connections 16"), which may be leads, catheters, or some other type of therapy delivery device. Therapy connections 16 may, as shown in FIG. 1, be leads implanted proximate to the spinal cord 18 of patient 14, and IMD 12 may deliver SCS therapy to patient 14 in order to, for example, reduce pain experienced by patient 14. However, the disclosure is not limited to the configuration of therapy connections 16 shown in FIG. 1 or the delivery of SCS therapy. For example, one or more leads may extend from IMD 12 to the brain (not shown) of patient 14, and IMD 12 may deliver deep brain stimulation (DBS) therapy to patient 14 to, for example, treat tremor, Parkinson's disease, or epilepsy. As further examples, one or more leads may be implanted proximate to the pelvic nerves, stomach, or other organs (not shown) and IMD 12 may deliver neurostimulation therapy to treat incontinence, gastroparesis, sexual dysfunction or other disorders.

Further, as discussed above, the disclosure is not limited to embodiments in which IMD 12 delivers stimulation therapy. For example, in some embodiments, IMD 12 may additionally or alternatively be coupled to one or more catheters or other substance delivery devices to deliver one or more therapeutic substances to patient 14, e.g., one or more drugs. Also, in some aspects, techniques for evaluating postures and activity states as described herein may be applied to IMDs that are generally dedicated to sensing or monitoring and do not include stimulation or other therapy components.

Additionally, this disclosure is not limited to implanted devices. Any implantable or external medical device may classify posture states for use in delivering therapy according to the techniques of the invention. Moreover, the techniques described herein may also be used for purposes other than delivering therapy. For instance, the posture state detection mechanisms described herein may be used for diagnostic purposes, such diagnosing a need for therapy, or determining how a patient is responding to existing therapy. Posture state detection may also be used to provide notifications, such as providing notification via a wireless link to a care giver that a patient has potentially experienced a fall. Thus, posture definition and classification according to the current disclosure may be used to initiate many types of actions.

In exemplary embodiments, IMD 12 may initiate actions in response to information within a record. For instance, a plurality of records may be stored in a table or another data structure. Each such record may describe at least one posture state and an associated action that is to be taken in response to detection of this posture state. As discussed above, a posture state is determined based on at least one of a posture and an activity state. When IMD 12 detects that a patient is in some predefined posture state, IMD 12 may automatically initiate the associated action for that posture state. This action may involve delivery of therapy according to a particular program, group of programs and/or a set of parameters. This action may alternatively or additionally involve providing some notification and/or recording some information. Other types of responses are possible.

In the illustrated example, system 10 also includes a programming device 20, which may, as shown in FIG. 1, be a handheld computing device. Programming device 20 allows a user such as a patient or a clinician to interact with IMD 12. Programming device 20 may, for example, communicate via wireless communication with IMD 12 using radio-frequency (RF) telemetry techniques, or any other techniques known in the art.

Programming device 20 may, as shown in FIG. 1, include a display 22 and a keypad 24 to allow the user to interact with programming device 20. In some embodiments, display 22 may be a touch screen display, and the user may interact with programming device 20 via display 22. The user may also interact with programming device 20 using peripheral pointing devices, such as a stylus or mouse. Keypad 24 may take the form of an alphanumeric keypad or a reduced set of keys associated with particular functions. In some embodiments, keypad 24 may include an increase amplitude button and a decrease amplitude button to directly adjust stimulation amplitude.

In exemplary embodiments, programming device 20 is a clinician programmer used by a clinician to define postures and posture states according to the current invention. The defined postures may then be used to detect postures and posture states that are assumed by the patient during daily life. The detected postures may be used to determine a type of therapy to provide to the patient, to monitor general well-being of the patient, to prescribe new therapies for the patient, and to determine whether the patient has undergone a posture-specific event such as suffering a fall.

Figure 2:
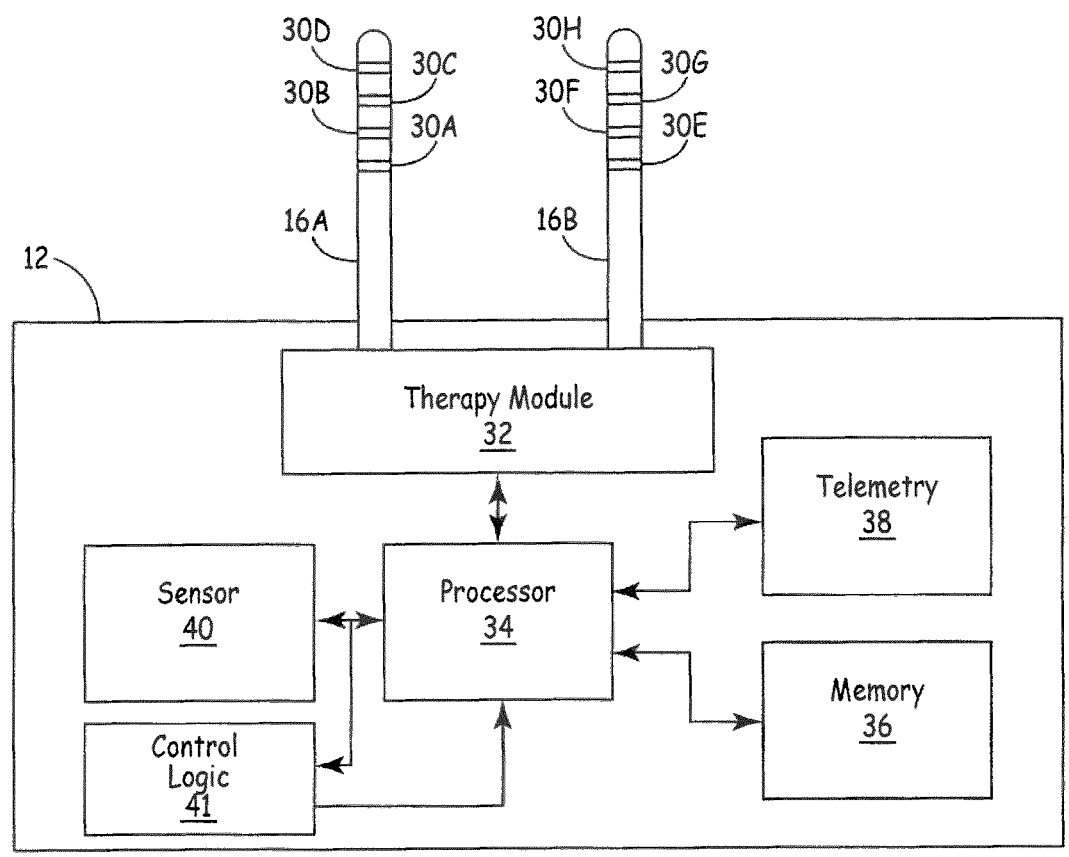
FIG. 2 is a block diagram illustrating one embodiment of an Implantable Medical Device in greater detail.

FIG. 2 is a block diagram illustrating one embodiment of IMD 12 in greater detail. IMD 12 may deliver neurostimulation therapy via therapy connections 16A and 16B. These therapy connections are shown to be leads having one or more electrodes 30A-H (collectively "electrodes 30"). They may alternatively include some other devices, such as one or more catheters for delivering a substance to a patient. IMD 12 may be coupled to any number of therapy connections. Therapy connections 16A and 16B are coupled to IMD 12 via therapy module 32. This may be a stimulation pulse generator, for example. Such a pulse generator may be coupled to a power source such as a battery. Therapy module 32 may deliver electrical pulses to patient 14 and/or may deliver some type of substance, such as a drug.

Therapy delivery may occur under the control of a processor 34. Processor 34 may comprise a microprocessor, a controller, a digital signal processor (DSP), an application specific integrated circuit (ASIC), a field-programmable gate array (FPGA), discrete logic circuitry, or any combination thereof.

Processor 34 may control therapy module 32 to deliver neurostimulation or other therapy according to a selected program. For instance, processor 34 may control therapy module 32 to deliver electrical pulses with the amplitudes and widths, and at the rates specified by the program. Processor 34 may also control therapy module 32 to deliver such pulses via a selected subset of electrodes 30 with selected polarities, e.g., a selected electrode configuration, as specified by the program.

IMD 12 also includes a telemetry circuit 38 that allows processor 34 to communicate with programming device 20. For example, a clinician may select programs, parameters, posture definitions, activity state definitions, other posture state definitions, and associated therapies and actions that are to be transferred to memory 36 of IMD 12. Processor 34 also communicates with programming device 20 to provide diagnostic information stored in memory 36 to a clinician via telemetry circuit 38. Processor 34 may also communicate with a patient programming device to receive therapy parameter adjustments or other therapy adjustments from a user such as patient 14, as well as commands to initiate or terminate stimulation. Telemetry circuit 38 may correspond to any telemetry circuit known in the implantable medical device arts.

IMD 12 further includes a sensor 40 to sense one or more parameters used to detect a posture state. In exemplary embodiments, sensor 40 includes a three-axis accelerometer, such as a piezoelectric and/or MEMs accelerometer. In other embodiments, multiple single or multi-axis accelerometers may be employed in place of one three-axis accelerometer. In yet other examples, sensor 40 may include gyroscopes or other sensors capable of sensing posture and/or activity levels. Thus, it will be understood that sensor 40 may comprise more than one sensor.

In exemplary embodiments, sensor 40 is located within a housing (not shown) of IMD 12. However, the disclosure is not so limited. In some embodiments, sensor 40 is coupled to IMD 12 via one or more additional connections such as leads (not shown). The sensor may be located anywhere within patient 14. In some embodiments, IMD 12 may be coupled to multiple accelerometer sensors located at various positions within patient 14 or on the external surface of patient 14, and processor 34 may receive more detailed information about the posture of, and activity undertaken by, patient 14. For example, one or more accelerometers may be located within/on the torso and at a position within/on a limb, e.g. a leg, of patient 14. In yet other embodiments, these one or more sensors may communicate wirelessly with IMD 12 instead of requiring one or more leads to communicate with the IMD. For example, sensor 40 may be located external to patient 12 and may communicate wirelessly with processor 34, either directly or via programming device 20.

As previously mentioned, sensor 40 senses one or more parameters that are used to detect and classify a posture state. A posture state is based on at least one of a posture and an activity state of a patient, where the activity state describes motion or activity of the patient. The activity state may relate to an overall activity level, an activity level in one or more selected directions, a vector associated with velocity or acceleration, and so on.

As an example, an Upright posture state may be defined to classify the position of a patient who is standing. This posture state definition need not take into account the patient's activity state, if desired. As another example, an Upright and Active posture state may be defined to describe a patient who is standing and who has undertaken an activity level that exceeds some predetermined threshold level. As yet another illustration, an Active posture state may be defined to describe a patient who exceeds some level of activity and without regard to the patient's posture. In this manner, sensor 40 may be used to detect a posture state associated with various types of postures and/or activity states.

IMD 12 also includes a memory 36, which may store programmed instructions that, when executed by processor 34, cause IMD 12 to perform the functions ascribed to IMD 12 herein. Memory 36 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like.

FIG. 2 may further include control logic 41. This control logic is provided in one embodiment to obtain and process the analog output of sensor 40. Control logic 41 may include discrete components, a microprocessor, a controller, a digital signal processor (DSP), an application specific integrated circuit (ASIC), a field-programmable gate array (FPGA), programmed instructions executable by one or more processors, or the like. Control logic 41 may operate alone, or in conjunction with processor 34, to process the sensor output for use in detecting a posture state. As an example, control logic 41 may process the raw signals provided by sensor 40 to determine activity counts indicative of activity level, velocity along one or more accelerometer axis, and so on, for use in detecting a posture state. As previously indicated, at least some of this processing may be carried out by processor 34 under control of programs stored within memory 36. Thus, control logic 41 may comprise any combination of hardware and/or programmed instructions.

Figure 3:
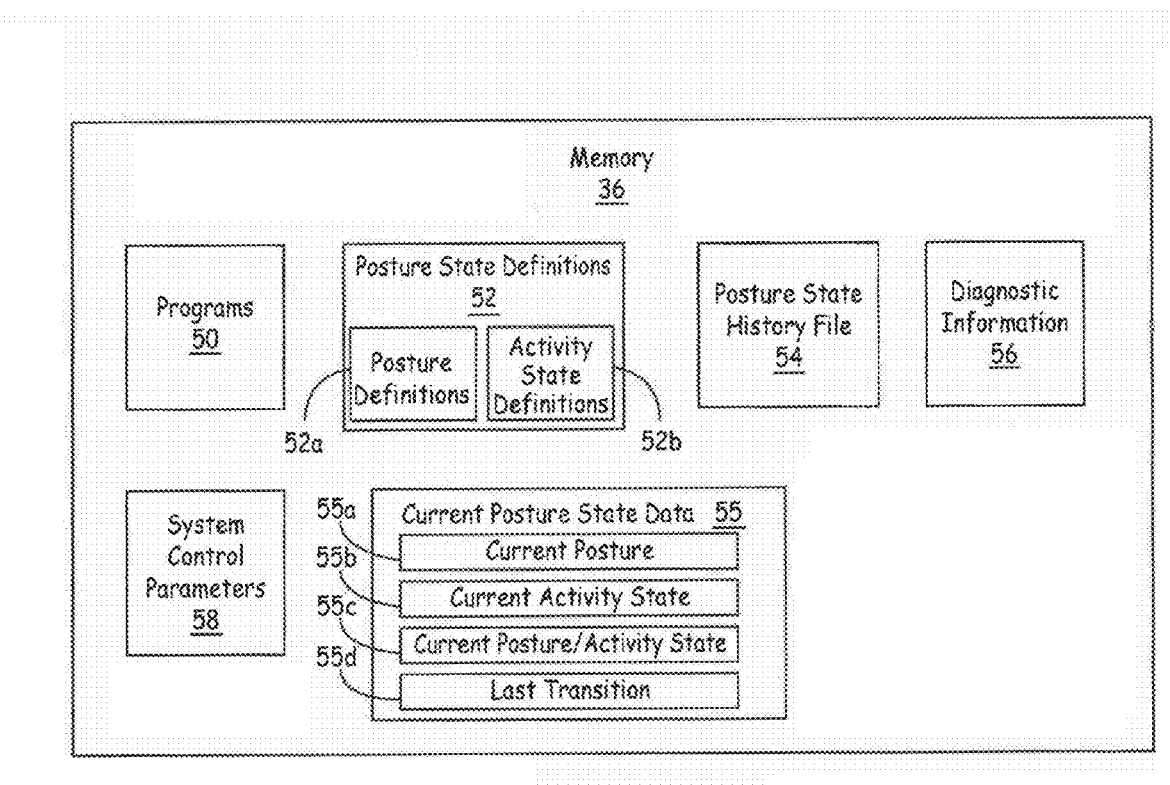
FIG. 3 is a block diagram illustrating an exemplary configuration of a memory of an Implantable Medical Device according to an embodiment of the disclosure.

FIG. 3 is a block diagram illustrating an exemplary configuration of memory 36 of IMD 12. As illustrated in FIG. 3, memory 36 stores programs 50, one or more of which processor 34 may employ to control therapy that is delivered to the patient. Some of programs 50 may be provided to take actions in response to classification of a patient's posture state. Programs 50 may also include those for controlling various aspects of processing signals of sensor 40 according to techniques described herein.

Memory 36 further stores posture definitions 52a and activity state definitions 52b, each of which is a subset of posture state definitions 52. In particular, a posture definition is a posture state definition that is defined only in terms of a patient's posture without regard to activity. An activity state definition is a posture state definition that is defined only in terms of a patient's activity without regard to posture. Other types of posture state definitions are defined in terms of both activity and posture.

A record of the posture states that have been assumed by the patient over time may be recorded in a posture state history file 54. In conjunction with this history file, information concerning the patient's current posture state may be maintained as current posture state data 55. This data may record, for instance, the patient's current posture 55a, current activity state 55b, current posture/activity state 55c, a most recent posture state transition 55d, and so on. This will be discussed further below.

Memory 36 may also store diagnostic information 56 for use in determining how a patient is responding to therapy, whether therapy modification is needed, whether therapy is to be initiated, and so on.

In one embodiment, system control parameters 58 may also be stored in memory 36. These parameters may be used to control, among other things, how signals from sensor 40 should be obtained and processed to classify a patient's posture state. These system control parameters 58 may, in one embodiment, be selected based on current posture state data 55. For instance, the parameters in use at a given time may be selected based on the posture state in which the patient was most recently classified, a posture state transition that a patient recently underwent, and so on. This will be described in detail below.

Figure 4:
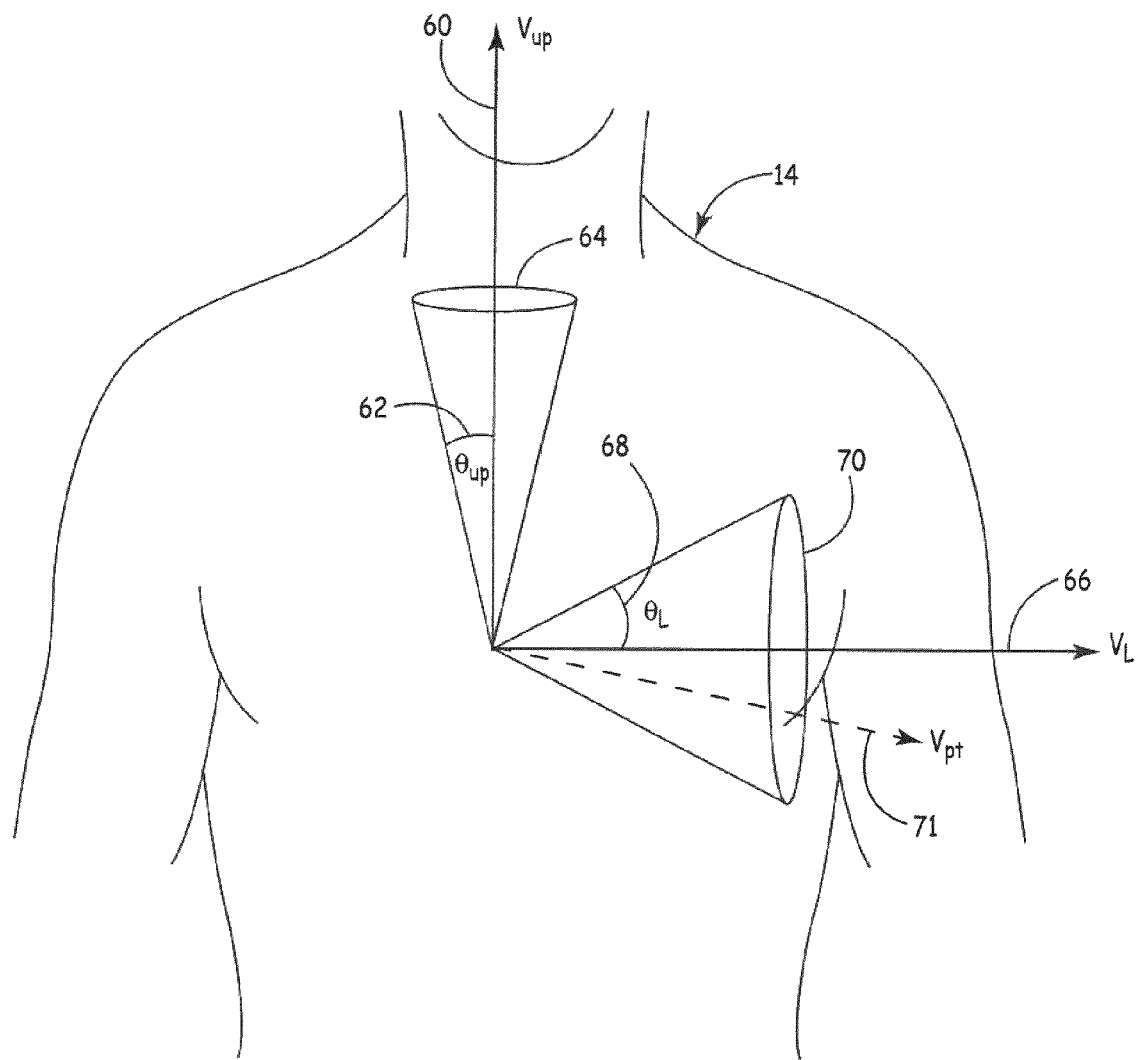
FIG. 4 is a graph illustrating one exemplary method of defining and classifying postures according to the current disclosure.

FIG. 4 is a graph illustrating one exemplary method of defining and classifying postures using sensor 40. Sensor 40 (not shown) is disposed in a fixed manner relative to patient 14. When patient 14 is known to be standing upright, sensor 40 will provide outputs that can be processed to obtain a vector $[V_1, V_2, V_3]$ which is shown as $V_{UP}$ 60. During a posture definition process, this vector may be associated with an Upright posture, as by storing some indication of the Upright posture along with one or more values identifying this vector. A tolerance may then be selected for this posture that describes a distance relationship to vector $V_{UP}$ 60. In the current example, the tolerance is an angle $\theta_{UP}$ 62 which may identify a maximum distance from vector $V_{UP}$ in any direction, as illustrated by cone 64. The vector $V_{UP}$ 60, which may be referred to as a defined posture vector, as well as the selected tolerance, which in this case is angle $\theta_{UP}$ 62, may be stored (e.g., in memory 36) in association with a posture definition for Upright. This definition may be stored as one of posture definitions 52a, for instance.

Once created in the foregoing manner, the definition for the Upright posture may be used to classify a patient's posture as follows. As the patient goes about daily life, one or more signals from sensor 40 may be acquired and optionally processed. Such processing may, for example, retain DC portions of the sensor signals for use in classifying a patient's posture. These signals may then be used to obtain a vector describing the patient's current posture. Such a vector may be referred to as a detected posture vector $V_{pt}$. This detected posture vector may be compared to defined posture vectors of posture definitions. For instance, this detected posture vector $V_{pt}$ that describes the patient's current posture may be compared to defined posture vector $V_{UP}$ for an Upright posture.

If a comparison between a detected posture vector $V_{pt}$ and a defined posture vector indicate that the detected posture vector satisfies the tolerance relationship indicated by the definition for the Upright posture, the patient will be considered to be in the Upright posture. For instance, in this case, if it is determined that the detected posture vector $V_{pt}$ lies within the cone 64 for the Upright posture as determined by the selected tolerance angle of $\theta_{UP}$ 62, the patient is classified as being in the Upright posture. This determination may be made using angles, or similarity metrics that may include trigonometric relationships (e.g., sine, cosine), other distance relationship such as city-block distances, and so on. According to this example, the patient may be leaning slightly forward, backward, or to either side of, vector $V_{UP}$, while still being categorized as being in the Upright posture so long as the detected posture vector lies within cone 64 defined by angle $\theta_{UP}$ 62.

In the specific examples of FIG. 4, the patient is classified as being in a posture if the detected posture vector $V_{pt}$ lies within an associated cone. In other examples, a patient may be classified as being in a posture if it is determined that a detected posture vector $V_{pt}$ lies outside of a cone that surrounds a defined posture vector. As previously described, these determinations may utilize angle comparisons, or similarity metrics involving trigonometric functions (e.g., sine, cosine), other distance relationship comparisons, and so on.

Example methods of comparing a detected posture vector to defined posture vectors are provided in patent applications entitled "Posture State Classification for a Medical Device", Ser. Nos. 12/433004 and 12/432,993, referenced above. The specific methods of comparing a detected posture vector to defined posture vectors are largely outside of the scope of the current disclosure, and other methods of using a vector to determine a patient's posture will be contemplated by those skilled in the art.

In a similar manner, other posture vectors may be defined. For instance, a vector $V_L$ 66 may be defined that will be used to determine a Left Side posture in which the patient 14 will be classified when he is lying on his left side. In a manner similar to that described above, a tolerance is defined for this vector that involves an angle $\theta_L$ 68. This angle may be used to describe a cone 70 defining a maximum distance from $V_L$ 66. When a detected posture vector lies within this posture cone 70, the patient 14 will be classified as lying on his left side.

In the foregoing manner, any one or more defined posture vectors may be selected for use in creating a posture definition. The posture definitions may each be associated with defined posture vectors that need not be in any particular plane or have in any relationship to any other posture vector.

In one embodiment, posture definitions may be created using patient participation. For instance, a patient may be requested to assume a posture, such as lying on his left side. While this posture is maintained, signals from sensor 40 may be obtained and processed in a certain manner. The resulting signal levels may be stored as a vector that is associated with a selected one of the posture definitions 52a, such as Left Side. The capture and storing of signals in this manner may be initiated by a user such as a clinician who is employing a user interface of programmer 20 (FIG. 1), for instance. The user may further employ programmer 20 to select a tolerance (e.g., the size of $\theta_L$) that is to be associated with the posture definition. In this manner, patient participation may be used to create a posture definition.

In other embodiments, one or more posture definitions may be pre-defined and pre-stored within an IMD or another device without use of patient participation. For instance, a device manufacturer or a clinician may create these definitions by selecting a vector and tolerance without the aid of the patient. These selected values may then be associated with a posture definition. Exemplary methods for creating and/or updating posture definitions and posture state definitions are provided in patent application "Reorientation of Patient Posture States for Posture-Responsive Therapy", Ser. No. 12/433,623, referenced above.

The foregoing provides some examples of how one or more signal from sensor 40 may be obtained and used as a detected posture vector $V_{pt}$ to classify a patient's posture. In a similar manner, signals from a sensor 40 may be used to classify a patient's activity state according to activity state definitions 52b (FIG. 3).

As one specific example of using signals to classify a patient's activity state, assume signals of sensor 40 may be processed to obtain an activity count that is indicative of an overall activity level of the patient. Further assume for exemplary purposes this count will range between 0 and 100. This activity level range may be incorporated into activity state definitions, as by associating certain subsets of this range with activity states. For instance, a low activity level of between 0-40 may be associated with an activity state definition of Inactive, and so on. Multiple such activity state definitions may be created.

In one example, activity state definitions 52b may be created using patient participation, as was described above in reference to creation of posture definitions 52a. For instance, a patient may be requested to undergo a specific activity, which may involve motion or lack thereof. While this activity is occurring, signals from sensor 40 may be obtained and processed in a certain manner. The resulting signal levels and/or associated signal level ranges may be stored as one of activity state definition 52b. The capture and storing of signals in this manner may be initiated by a user such as a clinician who is using programmer 20 (FIG. 1), for instance. In another example, activity state definitions may be pre-defined by device manufacturers, or may be defined by a clinician or some other user without employing patient participation.

Once activity state definitions are created in any of the foregoing ways, the definitions may be used to classify a patient's activity state. For instance, as a patient goes about daily life, signals from sensor 40 may be obtained and compared to the signal levels stored within the activity state definitions. As a specific example, assume signals from sensor 40 are obtained and processed to provide an activity count of the type described above. Assume further that in this example, the activity count detected from the patient is a value that lies within the range associated with the activity state definition of Inactive. Therefore, the patient in this case will be classified as being in an activity state of Inactive.

Other types of activity state definitions may be defined besides those associated with activity level. For instance, some such definitions may be defined that include a directional component, which may be expressed as a vector. Such a vector may indicate a direction of acceleration, a direction of velocity, or some other direction associated with motion. This vector may be stored in an activity state definition and thereafter compared to a vector obtained from a patient who is performing some activity. This comparison may be used to classify patient motion in a manner similar to that described above.

As previously described, posture definitions and activity state definitions are each sub-classes, or sub-sets, of posture state definitions. A posture state definition may reference a posture, an activity state, or both. As an example, an Upright and Active posture state definition may be created that takes into account activity state (i.e., Active) and posture (i.e., Upright). Signals from sensor 40 may be obtained and/or processed, and then compared to such posture state definitions to classify the patient's posture state.

In a manner similar to that described above, posture state definitions may be created using patient participation. In other cases, they may be created by clinicians or another user or provided by a device manufactured.

In all of the foregoing cases, signals from sensor 40 are obtained, processed, and compared against signal values stored in association with posture state definitions. This processing may be controlled by system control parameters 58. According to one aspect, one or more of the system control parameters 58 that are in use at a given time are selected. Selection may be controlled based on current posture state data 55 that describes a recent posture state classification for a patient. This is described in reference to the remaining drawings.

Figure 5:
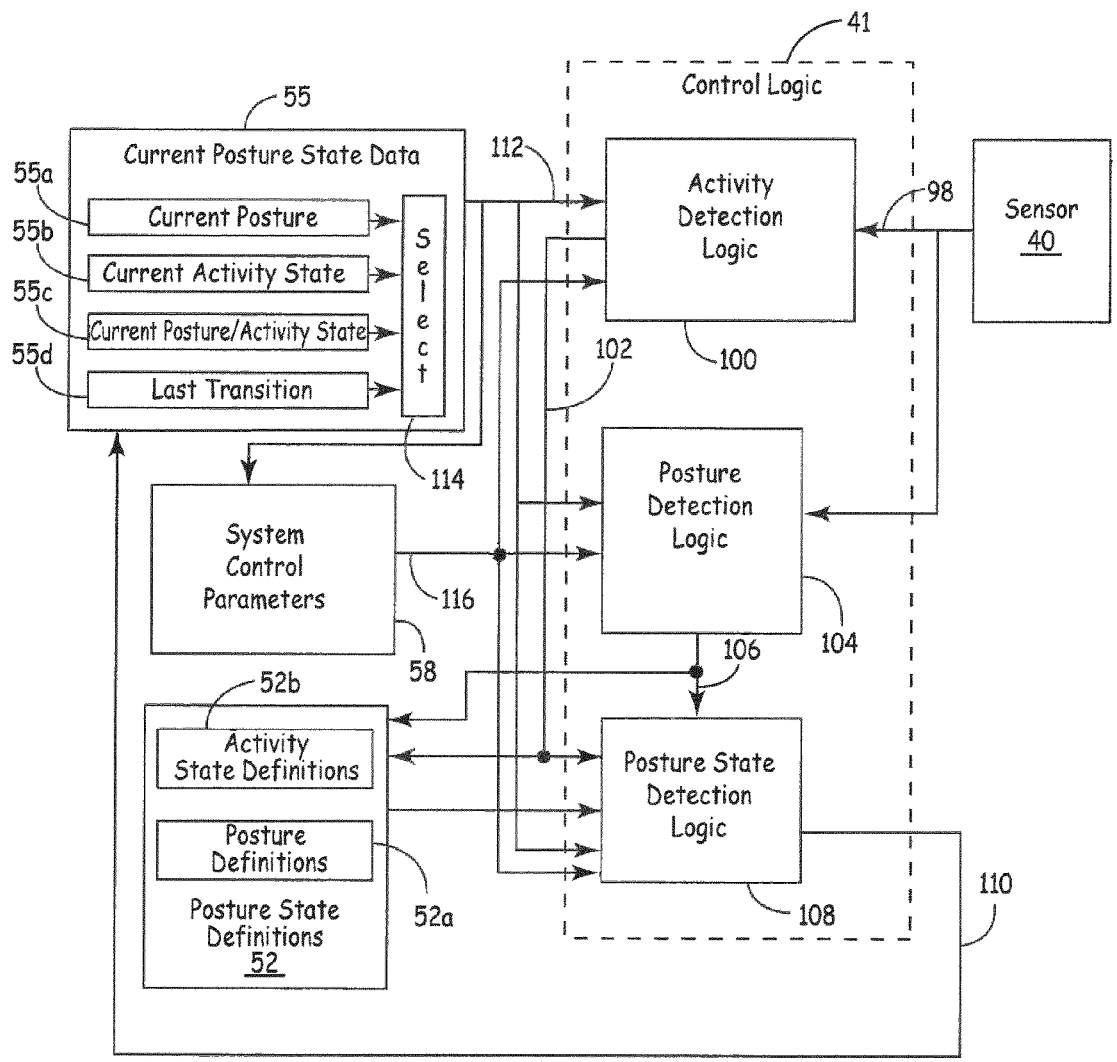
FIG. 5 is a functional block diagram illustrating how signals from sensor may be processed according to one embodiment of the invention.

FIG. 5 is a functional block diagram illustrating how signals from sensor 40 may be processed according to one embodiment of the invention. The signals from sensor 40 are provided to control logic 41 (shown dashed). This control logic embodies the functions that provide control for the system, and may be implemented in hardware, programmed instructions (as may be executed by processor 34), or any combination therefore. This logic is shown to include various sub-functions, such as activity detection logic 100, posture detection logic 104, and posture state detection logic 108.

Signals from sensor 40 are provided to control logic 41 on interface 98. As previously discussed, for purposes of this description, sensor 40 is assumed to be a three-axis accelerometer that provides x-, y-, and z-axis signals. These signals are provided to activity detection logic 100 for use in deriving activity signals 102 that will be used to classify the patient's activity state. In a like manner, sensor signals may be provided to posture detection logic 104 for deriving detected posture vector signals 106 that will be used to classify the patient's posture. Both the detected activity signals 102 and the detected posture vector signals 106 are provided to posture state detection logic 108 for use in classifying a patient's posture state. Classification may be accomplished by comparing these obtained signals to posture state definitions 52 in a manner described above.

Posture state detection logic 108 may provide an indication of the patient's current posture state classification. In one embodiment, this classification may be provided on interface 110. As one example, the classification provided on interface 110 may be a binary or a master-bitted code that identifies the patient's posture state, which is based on at least one of posture and/or activity state. Such an indication of posture state classification may be used to perform therapy adjustment and/or to initiate some other action, such as providing a notification, prompting storing of some data, etc.

According to the current disclosure, data on interface 110 is stored as current posture state data 55 (FIG. 3). In one embodiment, current posture state data 55 includes the current posture 55a, which identifies the posture of the patient (e.g., Upright). Current posture state data 55 may also include current activity state 55b, which describes activity/motion of the patient (e.g., Active).

Current posture state data 55 may, in one embodiment, also include current posture/activity state 55c. This value may identify a classification of the patient's posture state that is based on both posture and activity state, if such a definition has been created for use in the system (e.g., Upright & Active) and the current signals of sensor 40 match the requirements of this definition. If such a definition that references posture and activity state has not been created, and/or the sensor signals to not meet the criteria, in one embodiment, this current posture/activity state 55c may be set to a value of Unclassified. This is discussed further below.

Finally, current posture state data 55 may, in one embodiment, also identify a most recent posture state transition, shown as last transition 55d. The transition will reflect a most recent transition that occurred involving one of the current posture 55a, current activity state 55b, and current posture/activity state 55c. For instance, assume that current posture 55a now reflects an Upright posture. Before this current posture was recorded, current posture 55a reflected a Lying Down posture. Therefore, last transition 55d may identify the transition from a Lying Down posture to an Upright posture. Similarly, if current activity state 55b now identifies an Active activity state, but just prior to this, identified an Inactive activity state, last transition 55d may identify the transition from the Inactive to Active activity state. Finally, last transition 55d may indicate a transition that involved posture and activity, as identified by current posture/activity state 55c. For instance, if current posture/activity state 55c is currently set to Upright & Active, but was most recently set to Upright & Inactive, this transition may be reflected by last transition 55d. In one embodiment, a user may select which type of transition involving current posture state data 55 will be reflected by last transition 55d. In another embodiment, it may be hardcoded (e.g., always set to track a transition of current posture/activity state 55c.)

In one embodiment, the last transition 55d may identify the actual transition that occurred. For instance, in the case of a posture transition, a transition from Lying Down to Upright may be assigned a name Lying/Upright that is recorded as the last transition 55d. In another embodiment, this transition may be recorded by storing the previous posture, which in this case is Lying Down, as the last transition 55d. Since the current posture of Upright is recorded as current posture 55a, the transition may be determined by comparing the last transition 55d with the current posture 55a. A similar type of operation may occur when either the current activity state 55b or current posture/activity state are being tracked by the last transition.

As may be appreciated from the foregoing discussion, the patient may be in multiple posture states at once. For instance, at the same time the patient is in an Upright and Active posture state per current posture/activity state 55c, the patient may also be classified in the Upright posture state that is based only on the patient's upright position per current posture 55a. The patient may at the same time be in the Active posture state that is based only on the patient's activity level per current activity state 55b.

At any given time, the patient's current posture and/or activity state may be Unclassified. For instance, the current posture 55a will be identified as Unclassified if the signals indicative of posture do not meet the requirements of any of the posture definitions 52a. As a specific example, assume that in FIG. 4, only the Upright and Left Side posture definitions have been created. Further assume the patient's detected posture vector $V_{pt}$ 71 obtained from sensor 40 is outside of cones 64 and 70 such that the patient's current posture does not meet the requirements of either posture definition. In this case, the patient's posture will be classified as Unclassified. Similarly, a patient's activity state will be Unclassified if the signals indicative of activity do not meet the requirements of any of the activity state definitions 52b. Likewise, if both the patient's current posture and activity state as indicated by sensor signals do not meet the requirements of any of the posture state definitions that involve both posture and activity state, current posture/activity state 55c will be set to Unclassified. Finally, last transition 55d may be Unclassified if either the previously-recorded data or the current data associated with the field that is being tracked for transition purposes is Unclassified.

In the foregoing manner, current posture state data 55 may identify the patient's current posture, current activity state and/or a current posture/activity state. Current posture state data 55 further identifies a last posture state transition 55d. This transition will be based on not only the current posture/activity state 55c, but the posture state in which the patient was classified prior to being classified in the current posture state.

Current posture state data 55 may be provided on interface 112 to control how activity detection logic 100, posture detection logic 104, and posture state detection logic 108 process signals from sensor 40. This will be discussed in detail below. This allows control logic to process signals from sensor 40 based on a current posture 55a, current activity state 55b, a current posture/activity state 55c, and/or a last posture state transition 55d. Select circuit 114 is, in one embodiment, programmable to allow the signals that are forwarded onto interface 112 to be selected to include one or more of the data types stored by current posture state data 55, including current posture 55a, current activity state 55b, a current posture/activity state 55c, and/or a last posture state transition 55d.

FIG. 5 also shows the system control parameters 58. As discussed previously, these parameters may, in one embodiment, further control how the various logic blocks of control logic 41 operate. One or more of the system control parameters 58 that are in use in the system at a given time may be selected via the signals on interface 112 from current posture state data 55. The system control parameters that are selected in this manner may be provided on interface 116 to control logic 41 for use in controlling how signals of sensor are processed and how a posture state is classified and used.

Before continuing, it is noted that the logic of FIG. 5 may be implemented in any combination of hardware (including discrete components, one or more processors, or any other type of circuitry), programmed instructions, or a combination of hardware and programmed instructions. Moreover, the manner in which the logic is partitioned in FIG. 5 is largely arbitrary, and is selected to aid in the discussion of the functionality. However, partitioning may occur in other ways. For instance, all of the logic of FIG. 5 may be combined into a single logic block. As another example, activity detection logic 100 and posture detection logic 104 may be combined. Many such combinations may be contemplated. Thus, FIG. 5 should not be interpreted as limiting the disclosure to any specific implementation or partitioning of the logic, as many embodiments may be obtained by those skilled in the art.

Figure 6:
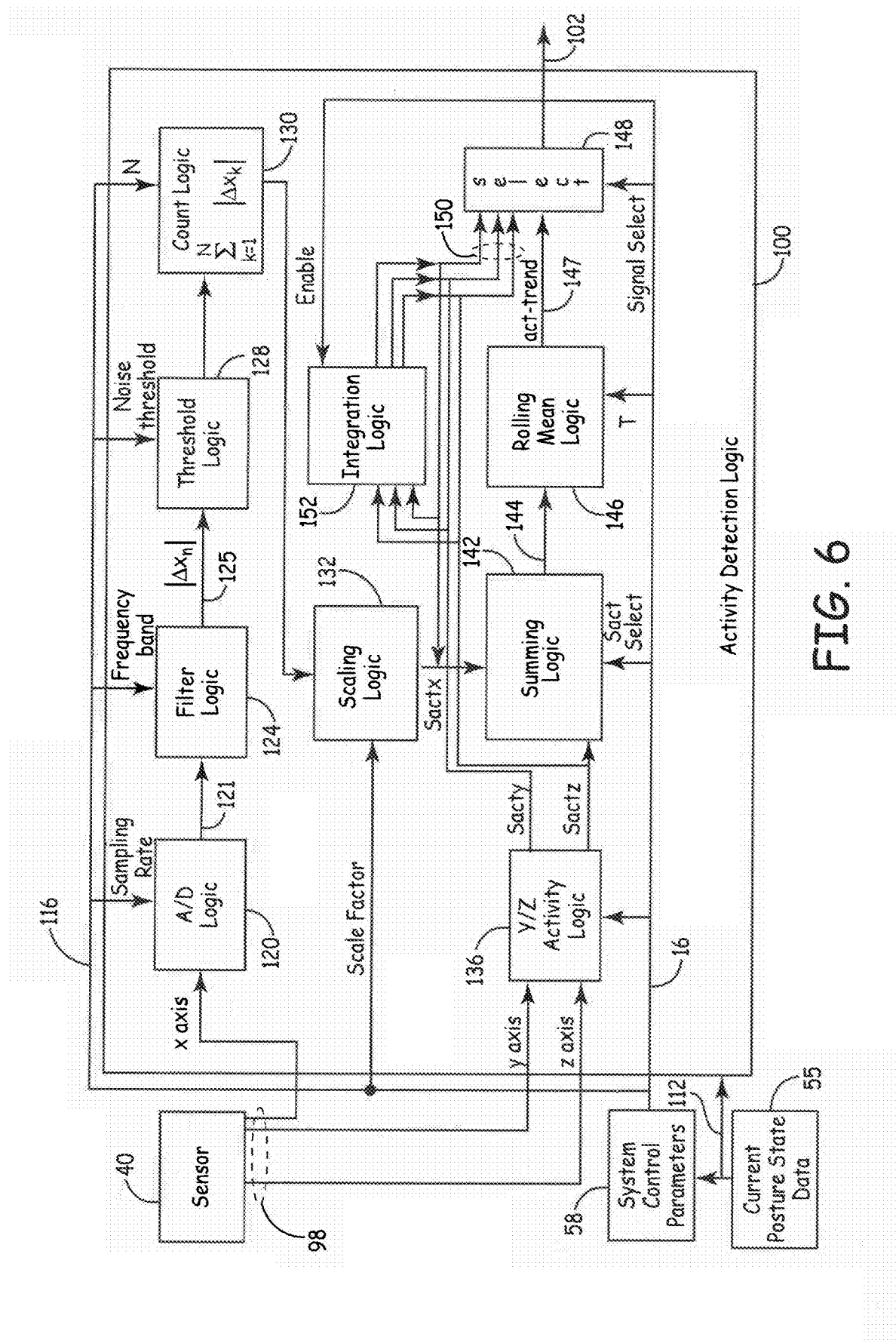
FIG. 6 is a functional block diagram of one embodiment of activity detection logic.

FIG. 6 is a functional block diagram of one embodiment of activity detection logic 100. This logic receives x-, y-, and z-axis signals from sensor 40. In the current example, these signals will be processed to generate one or more signals represented by interface 102 that will be used by posture state detection logic 108 for posture state classification. In the current exemplary embodiment, the system of FIG. 6 will be described as generating a signal indicative of overall activity level (e.g., footfalls) of a patient. However, the system may be readily adapted to generate other types of signals for use in classifying a patient's activity, such as a vector that describes a direction of velocity or acceleration. This is discussed further below.

The system of FIG. 6 may be used in at least two ways. This system may be employed when initially acquiring values for use in creating activity state definitions. For instance, a patient may be asked to begin some activity so that a particular signal level value may be measured and provided on interface 102 to be stored as an activity state definition 52b. In addition, the system of FIG. 6 may be used to classify a patient's activity state during day-to-day life. When used in this capacity, the signals shown on interface 102 are provided to posture state detection logic 108, which compares the previously-created posture state definitions to these measured signals to classify the patient's posture state, as will be described in detail.

According to the current disclosure, one or more of the various logic blocks shown in FIG. 6 may each operate in a selectable manner. The selection may be made based directly on the current posture state data 55 that is provided via interface 112. Additionally or alternatively, the selection may be made based on system control parameters 58 that are, in turn, selected via the current posture state data 55. These system control parameters 58 are provided via interface 116. Because each of the logic blocks in FIG. 6 may operate in a selectable manner based on current posture state data 55, the way in which sensor signals 40 are processed is determined based on a current posture state or a recent transition between two posture states, wherein a posture state may involve a posture, an activity state, or both. This allows signal processing to be carried out in a more optimized manner that is tailored to a patient's current posture and/or activity or to a recent transition between a previous posture and/or activity and a current posture and/or activity.

The signals from sensor 40 are provided on interface 98 (shown dashed) to activity detection logic 100. The x-axis signal is provided to A/D logic 120, and the y-axis and z-axis signals are provided to logic block 136 to be described below.

In this embodiment, the x-axis signal is an analog signal indicative of acceleration along an x-axis of sensor 40. A/D logic 120 performs analogue-to-digital (A/D) conversion of this signal, and may also perform some type of signal adjustment related to sensor calibration. For instance, calibration of sensor 40 during system initialization may have revealed the need to apply an additive offset and/or a scaling factor to the x-axis signal.

A/D logic 120 provides signal samples on interface 121 indicative of acceleration along the x-axis of sensor 40. These samples may be obtained at a sampling rate that is determined by the signals shown on interface 116 received from system control parameters 58. As previously described, this sampling rate may be selected based on the current posture state data 55. As one specific example, the sampling rate may be increased if the patient is determined to be in a posture state that involves a higher level of activity, or if the patient recently underwent a particular posture state transition, such as transitioning from a bending over position to an upright position, or transitioning from a low activity level directly to a high activity level, skipping intermediate activity levels. For instance, the sampling rate may be increased from 12.5 Hz to 25 Hz.

As yet another example, it may be beneficial to lower the sampling rate when a patient is in certain posture states, such as states that involve postures wherein a patient is lying down and/or inactive, as occurs during sleep. This may help conserve power, which is important in power-limited applications such as IMDs. The number of possible sampling rates and posture states in use in the system at a give time may depend on a user, such as clinician, and may be selected via programmer 20, if desired.

The signal samples on interface 121 are provided by A/D logic 120 to filter logic 124. In one embodiment, filter logic 124 is a programmable filter that may be implemented in hardware and/or software, and that can be tuned to extract a frequency range of interest based on the current posture state data 55. For instance, it may be known that if the patient is currently in a defined Running posture state (a posture state that, for example, may have been defined while a patient was running), the activity signal of interest will primarily be expressed within a frequency band ranging from frequency f1 to frequency f2, whereas other types of activities may involve other frequency bands. To optimize signal processing, system control parameters 58 provided on interface 116 indicate a frequency range based on the current posture state data 55. This range will be used to tune filter logic 124 to extract the appropriate signals.

In general, for extraction of a signal indicative of activity, filter logic 124 will perform high-pass filtering of the samples from interface 121 using the selected frequency range. This filtering will produce filtered signal samples on interface 125. Each such sample may, in one embodiment, be represented as $|\Delta X_n|$ because the sample substantially approximates the absolute value of a difference between a DC signal value and the current digital value provided on interface 121.

Threshold logic 128 receives the samples from interface 125 and eliminates the samples that are below a selected noise threshold. For instance, a sample that is less than some predetermined value will be replaced with a value of "0" so that the effects of noise on the signal are reduced. In one embodiment, the current posture state data 55 may determine this noise threshold.

The signals provided by threshold logic 128 are supplied to count logic 130, which is logic that will obtain the sum of N consecutive samples, $|\Delta X_n|$. For instance, assuming sampling occurs as 25 Hz, N may be set to 25, so that count logic provides the sum of the samples $|\Delta X_n|$ that are obtained in one second. This sum may be referred to as an "activity count". The number "N" of consecutive samples may be selected by system control parameters 58 based on the current posture state data 55, if desired. Alternatively, "N" may be replaced by a time period T (e.g., 1 second) over which the sum is to be generated.

The activity count for the x-axis, "actx", which is produced by count logic 130, may be supplied to scaling logic 132. This optionally scales the activity count, as may be needed to store that count in a predetermined amount of storage space. For instance, assume that each activity count is to be allocated a byte of storage space. The scale factor may be selected to ensure that each activity count may be expressed as an eight-bit value. The scale factor may also be used to change the relative important between the x-axis activity count and a similar value derived for the y-axis and/or z-axis. The scale factor used by scaling logic 132 may be provided by system control parameters 58 based on current posture state data 55, if desired.

The scaled activity count for the x-axis signal, sactx, is provided to summing logic 142. Summing logic also receives scaled activity counts that are derived for the y-axis, and z-axis sensor signals, shown as sacty, and sactz, respectively. The scaled activity counts sacty and sactz are generated via logic block 136 using a mechanism similar to that shown and described for the generation of the scaled activity count sactx obtained for the x-axis. That is, each of logic blocks 120-132 may be provided to process each of the y-axis and z-axis signals from sensor 40, if desired. Alternatively, only some of the logic blocks shown for x-axis processing may be provided for the y-axis and z-axis signals. These additional logic blocks are not shown individually for ease of reference and are represented by Y/Z activity logic 136. As was the case with the processing of the x-axis signal, each such logic block may receive parameters on interface 116 for use in controlling signal processing. In another embodiment, one or more of the x-, y-, or z-axis signals may not be used and may be eliminated from the processing entirely. In another scenario, more than three sensor signals may be processed in a manner similar to that shown for the x-axis signal and used to classify a patient's posture state.

According to the current embodiment, summing logic 142 may receive up to three signals including sactx, sacty, and sactz. Summing logic 142 may forward one of the scaled activity count signals onto interface 144, or may instead obtain a sum of two or three of the signals which is forwarded to interface 144. Whether a single signal or a sum of signals is forwarded onto interface 144, and which signal(s) are used to produce a sum, may be determined by current posture state data 55 via information provided on interface 116. For instance, if the patient is in an Upright posture state corresponding substantially to a z-axis of sensor 40, it may be desirable to include only the sactz is the signal provided to interface 144. In some cases, if the patient is active and in a posture substantially occupying a plane corresponding with the x-axis and y-axis of sensor 40, it may be desirable to add samples sactx and sacty to produce a sum of samples that is provided to interface 144. Alternatively, there may be some situations wherein the patient's overall activity state provides the most information, and therefore all three of the scaled activity count values may be added to produce the signal on interface 144. The way in which these three signals are used to generate the signal on interface 144 may be dependent on the current posture state data 55, as indicated by the sact select signal provided via interface 116 to summing logic 142.

The signal on interface 144 is provided to rolling mean logic 146. As may be appreciated, this signal comprises a sequence of signal samples. This signal may be smoothed by rolling mean logic 146 by obtaining, for each new sample, an average value that takes into account the value of the most recent sample as well as the values of the previous T-1 consecutive samples that preceded the most-recent sample. The signal smoothing capability provided by rolling mean logic 146 may be beneficially employed to detect periods of sustained activity. As an example, a patient may be walking vigorously for some extended period of time. During this period of high activity, the patient may stop momentarily, as to tie a shoe lace, for example. The patient may then resume a brisk walking pace. By proper selection of the parameter T, the rolling mean logic 146 will allow the system to continue to detect a high overall activity level despite the brief cessation of activity that occurs between otherwise active periods. In this manner, rolling means logic 146 provides "trend" data that may be employed to determine the start time, duration, and intensity associated with patient activity. Use of this trend data will generally result in a more accurate reflection of a posture state than would otherwise be achieved by processing that considers each sample in isolation.

Parameter T used to generate the rolling means may be selected by system control parameters 58 based on a currently-detected posture state data 55. This parameter T may be a larger value, for instance, if a current posture state data 55 reflects that the patient is undergoing a high level of activity, or if a most recent posture state transition involved an abrupt level change in activity (e.g., high-to-low or low-to-high transition, without any intermediate transition.)

Rolling mean logic 146 provides an activity trend signal, act_trend, to select logic 148, which may forward this signal to interface 102 to posture state detection logic 108 for use in classifying a patient's posture state. Control of select logic 148 may be provided by system control parameters 58 and/or current posture state data 55.

In the above-described examples, the various logic blocks receive control signals from system control parameters via interface 116. In an alternatively embodiment, one or more of the logic blocks shown in FIG. 6 may additionally or alternatively receive control signals directly from current posture state data 55. Such a signal received from current posture state data 55 may directly select between one of multiple operating modes. As an example, A/D logic 120 may have a selectable setting that chooses the sampling rate based on one or more signals provided on interface 112 directly from current posture state data 55. This may be instead of, or in addition to, the A/D logic 120 receiving a sampling rate on interface 116 from system control parameters 58. Any or all of the logic blocks of FIG. 6 may be configured in this manner such that they are additionally or alternatively controlled directly by current posture state data 55.

The above-described example illustrates how activity detection logic 100 utilizes signals from sensor 40 to derive a value for an activity trend signal, act_trend. This trend signal may be based on any one or more of the three signals received from sensor 40, as selected by the current posture state data 55 and/or system control parameters 58. The invention is not limited to derivation of an activity trend signal, however. The concepts described herein may be applied to derivation of other types of activity signal. For instance, each of the signals sactx, sacty, and sactz may be forwarded via interface 150 (shown dashed) to select logic 148 and forwarded to interface 102 for use as a vector indicative of the acceleration. This selection of the vector rather than the activity trend signal may be controlled by the signal selection control line provided to select logic 148 via interface 116. Alternatively, only one or two of the sactx signals on interface 150 may be selected for forwarding onto interface 102. Thus, control over which activity signals are forwarded to interface 102 may be exercised based on system control parameters 58 and/or current posture state data 55.

Alternatively or additionally, integration logic 152 may be provided to integrate one or more of the sactx, sacty, and sactz signals. If desired, one, two, or all three of the integrated signals may be selectively driven onto interface 150 for selection by select logic 148. The control to select the signals in this manner may be based on system control parameters 58 and/or current posture state data 55. These integrated signals may be used to determine velocity. If all three such signals are provided to interface, a vector indicative of velocity is available for use in classifying the patient's posture state. Thus, the signals of sensor 40 may be processed and/or combined in many different ways according to the current invention, and the processing steps described herein are merely exemplary. Any one or more of the processing steps may be controlled by current posture state data 55 and/or by system control parameters 58, and the selection of signals provided to interface 102 may likewise be controlled in this manner.

It will be appreciated that the logic blocks of FIG. 6 are discussed in terms of their functionality. The described functions may be performed solely in hardware. Alternatively, many of the functions may be implemented via programmed instructions, such as software and/or firmware instructions that are stored within a storage device such as memory 36 and executed by a processor such as processor 34 or some dedicated processor included within control logic 41. Any combination of hardware or programmed instructions may be used to implement the functions. Additionally, the functions may be performed entirely within IMD 12 as by control logic 41, or may be partially performed by an external device such as a clinician programmer 20, a patient programmer, a personal computer, or another external device. For instance, some of the logic blocks 120 through 146 may be implemented external to IMD 12 in a device such as clinician programmer 20 or a personal computer based on signals provided to this external device via a communication session. One or more signals obtained during such external processing may then be re-transmitted to IMD 12 to continue processing within the IMD.

In addition, it may be understood that the system control parameters 58 and/or current posture state data 55 may be provided to the various logic blocks in many different ways. For instance, an interface (e.g., bus, point-to-point, etc.) may directly connect one or more logic blocks shown provided by activity detection logic 100 with a storage device storing system control parameters 58 and current posture state data 55. Such an interface may correspond to interfaces 116 and 112 of FIG. 6, for instance. However, this is merely one mechanism for providing this communication, and is illustrated for discussion purposes only. In other embodiments, there need not be any direct interface between system control parameters 58, current posture state data 55, and/or the logic blocks of FIG. 6. Instead, communication may occur via a processor such as processor 34 which retrieves parameters and data values from a memory such as memory 36, and provides the values to the appropriate logic blocks under program control. As yet another example, if a logic function is implemented in software or other programmed instructions, a processor may retrieve system control parameters 58 and current posture state data 55 during execution to control how processing for the function will be carried out. Thus, it will be understood that the functionality represented by interfaces 112 and 116, and indeed the functional blocks of FIG. 6 generally, is intended to illustrate that control is exerted over the various signal processing capabilities using the system control parameters 58 and/or current posture state data 55. This depiction is not intended to limit the way this control is exerted, which may be implemented using many mechanisms.

In some embodiments of FIG. 6, logic blocks may be eliminated. For instance, scaling logic 190 may not be needed in some systems wherein the signal generated by count logic 188 does not require any additional scaling. In some scenarios, the configuration of the logic blocks may be rearranged. For instance, if a hardware filter is being utilized rather than a software filter, filter logic 124 may be adapted to receive and process an analog signal and then provide this filtered signal to A/D logic 120. Thus, the arrangement of the logical functional relative to each other is to be considered merely exemplary, and not limiting.

Figure 7:
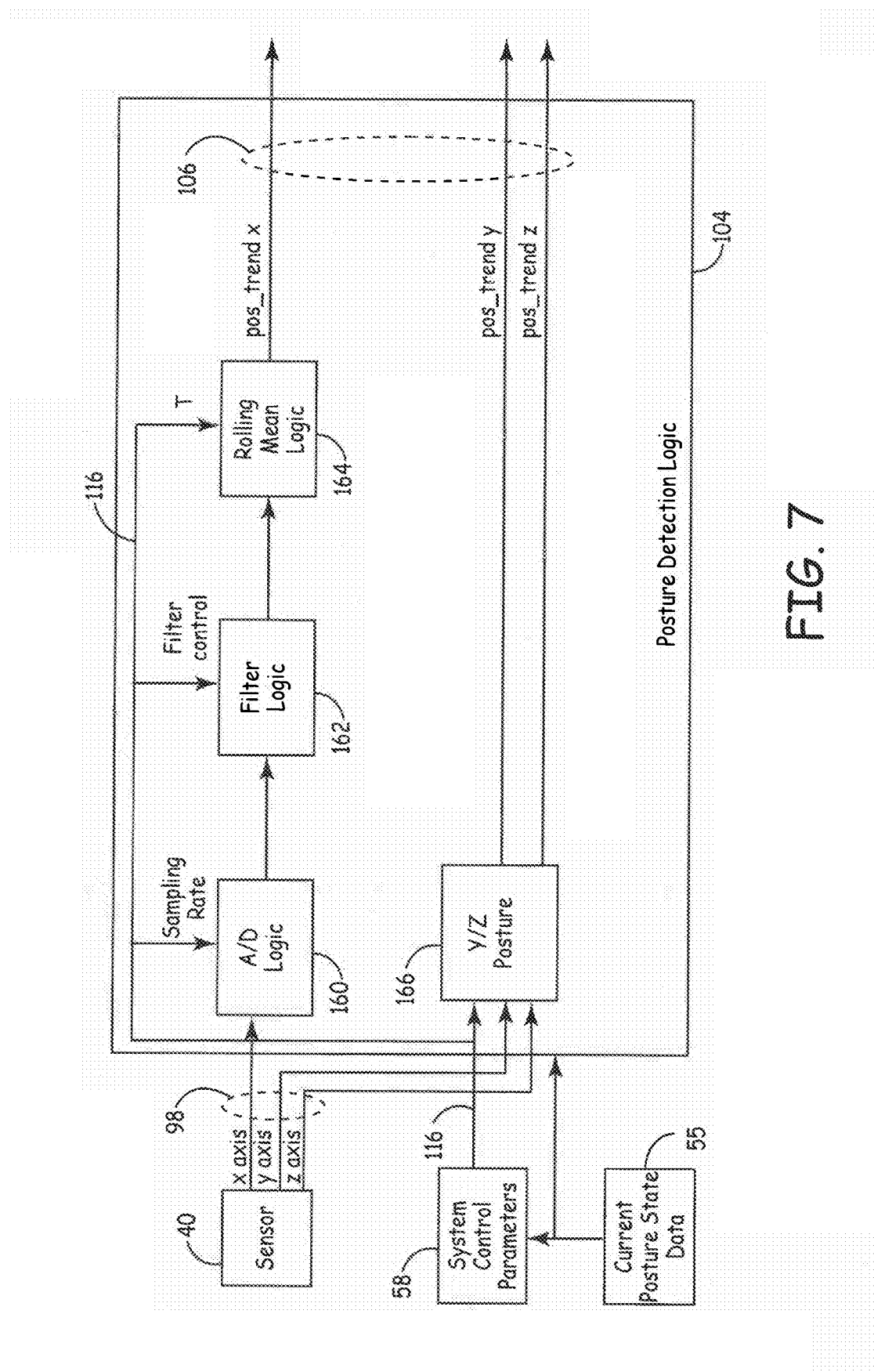
FIG. 7 is a functional block diagram of one embodiment of posture detection logic.

FIG. 7 is a functional block diagram of one embodiment of posture detection logic 104. This logic receives x-, y-, and z-axis signals from sensor 40 and generates one or more signals indicative of posture. The system of FIG. 7 may be used in at least two ways. This system may be employed when initially acquiring vectors for use in creating posture definitions. For instance, a patient may be asked to begin some activity so that a particular signal level value may be measured by sensor 40, processed according to the logic shown in FIG. 7, and the resulting signals are provided on interface 106 (shown dashed) to be stored along with a posture definition 52a.

After one or more posture definitions are created, the system may be used to classify a patient's posture during day-to-day life. When used in this capacity, signals from sensor 40 are processed to generate one or more signals indicative of the patient's current posture. These signals are provided on interface 106 to posture state detection logic 108, which compares the signals to the signal values contained in the previously-created posture state definitions and thereby classifies a patient's posture.

As was the case with the system of FIG. 6, one or more of the logic blocks shown in FIG. 7 may each operate in a selectable manner that is controlled by the current posture state data 55 that is provided via interface 112. Additionally or alternatively, the selection may be made based on system control parameters 58 that are, in turn, selected via the current posture state data 55.

According to the system of FIG. 7, sensor 40 provides x-, y-, and z-axis signals to posture detection logic 104. In particular, the x-axis signal is shown being provided to A/D logic 160, which performs analog-to-digital (A/D) conversion on the signal. This logic block may also perform some type of signal adjustment or scaling related to sensor calibration in a manner similar to that described above in regards to logic block 120 of FIG. 6.

A/D logic 160 provides system samples indicative of acceleration occurring along the x axis of sensor 40. In a manner similar to that described above, the samples may be obtained at a sampling rate determined by system control parameters 58 as provided on interface 116, which may be selected based on the current posture state data 55 for the patient.

Signal samples are provided by A/D logic 160 to filter logic 162, which is a filter implemented in hardware and/or software that may operate according to parameters provided on interface 116 from system control parameters 58. In one embodiment, filter logic 162 is a low-pass filter to extract a DC portion, or some other low-frequency portion, of the signal. The signal frequencies that are extracted may be selected by the signals provided via interface 116.

Another implementation of this filter obtains an average for N consecutive samples. This average minimizes the AC variations that have occurred over those N samples. As an example, assume A/D logic 160 provides samples to filter logic 162 at a rate of 25 Hz. Filter logic 162 may be adapted to generate an average for each group of 25 samples, thereby providing averaged signal samples at a rate of 1 Hz. In this embodiment, the number of samples N utilized by filter logic 162 to obtain a single averaged sample is a filter control signal that may be selected by system control parameters 58 based on current posture state data 55.

A software implementation of filter logic 162 as described above may be advantageously employed in devices that seek to conserve power. In other implementations, any other type of filter logic may be employed instead of this type of filter. Filter logic 162 may also include noise filtering capabilities.

Filter logic 162 provides signal samples to rolling mean logic 164. Rolling mean logic 164 is adapted to smooth the received signals by obtaining, for each received signal sample, a rolling average value that takes into account the value of the most recently-received sample as well as the values of the previous T-1 consecutive samples that preceded the most-recent sample. This generates a trend signal, pos_trendx. The value for T may be selected by data provided on interface 116. Alternatively, the value T may be replaced by a selected time period over which the rolling means is to be generated.

Similar processing may be performed for the y- and z-axis signals. That is, one or more of logic blocks 160-164 may be provided for each of the y- and z-axis signals. These logic blocks are not shown individually for ease of reference and are represented by Y/Z posture logic 166. As was the case with the processing of the x-axis signal, each such logic block may receive parameters on interface 116 for use in controlling signal processing. In this manner, the signal processing is tailored to the current posture state data 55. As an example, it may be desirable to decrease sampling rate and increase the number of samples N and time T that is used to generate the posture trend signals when the patient is relatively inactive. This will conserve power and result in adequate posture classification accuracy. Conversely, it may be desirable to increase sampling rate, and decrease N and T during periods of high activity. Many uses are possible, and these are only examples.

It will be appreciated that the logic blocks of FIG. 7 are discussed in terms of their functionality. The described functions may be performed solely in hardware. Alternatively, many of the functions may be implemented via programmed instructions, such as software and/or firmware instructions that are stored within a storage device such as memory 36 and executed by a processor such as processor 34 or a dedicated processor, as may be provided by control logic 41. In another embodiment, any combination of hardware or programmed instructions may be used to implement the functions. Additionally, the functions may be performed entirely within IMD 12 as by control logic 41, or may be partially performed by an external device such as a clinician programmer 20, a patient programmer, a personal computer, or another external device using telemetry communication. In some embodiments of FIG. 7, logic blocks may be eliminated or the logic may be re-ordered. For instance, it may not be necessary to obtain a rolling mean for some applications, and thus rolling mean logic 164 and the y-axis and z-axis counterpart logic may be eliminated. In another embodiment, additional logic blocks may be introduced within the scope of the disclosure. What is important to note is that any or all of the logic blocks may be controlled, at least in part, by system control parameters 58 selected based on the current posture state data 55.

As was the case in the system of FIG. 6, if desired, some or all of the logic blocks of FIG. 7 may receive control signals from current posture state data 55 directly to determine an operating mode. For instance, A/D logic 160 may have several predetermined sampling rates that are selected by a current posture state indicated on interface 112. These signals may be provided in addition to, or instead of, a sampling rate indication provided on interface 116 by system control parameters 58.

In addition, it may be understood that the system control parameters 58 and/or current posture state data 55 may be provided to the logic blocks in many different ways. For instance, some type of interface may directly connect one or more logic blocks with a storage device storing system control parameters 58 and/or current posture state data 55. Such interfaces may be represented as interfaces 116 and 112 of FIG. 7, for example. However, this is merely one mechanism for providing this communication, and is illustrated for discussion purposes only. In other embodiments, there need not be any direct interface between system control parameters 58, current posture state data 55, and/or the various logic blocks of FIG. 7. Instead, communication may occur via a processor such as processor 34 which retrieves parameter and data values from a memory such as memory 36, and provides the values to some or all of the appropriate logic blocks under program control. Alternatively or additionally, the parameters and/or data may be utilized to control software execution. Thus, it will be understood that the functionality represented by interfaces 112 and 116, and indeed the functional blocks of FIG. 7 generally, is intended to illustrate that control may be exerted over the signal processing function using the system control parameters 58 and current posture state data 55. This depiction is not intended to limit the way in which this control may be exerted. Moreover, those skilled in the art will contemplate other processing functions that may be used to process signals of sensor 40 for posture classification, ones of which may be controlled based on current posture state data 55. Thus, the illustrated system is exemplary only.

Figure 8:
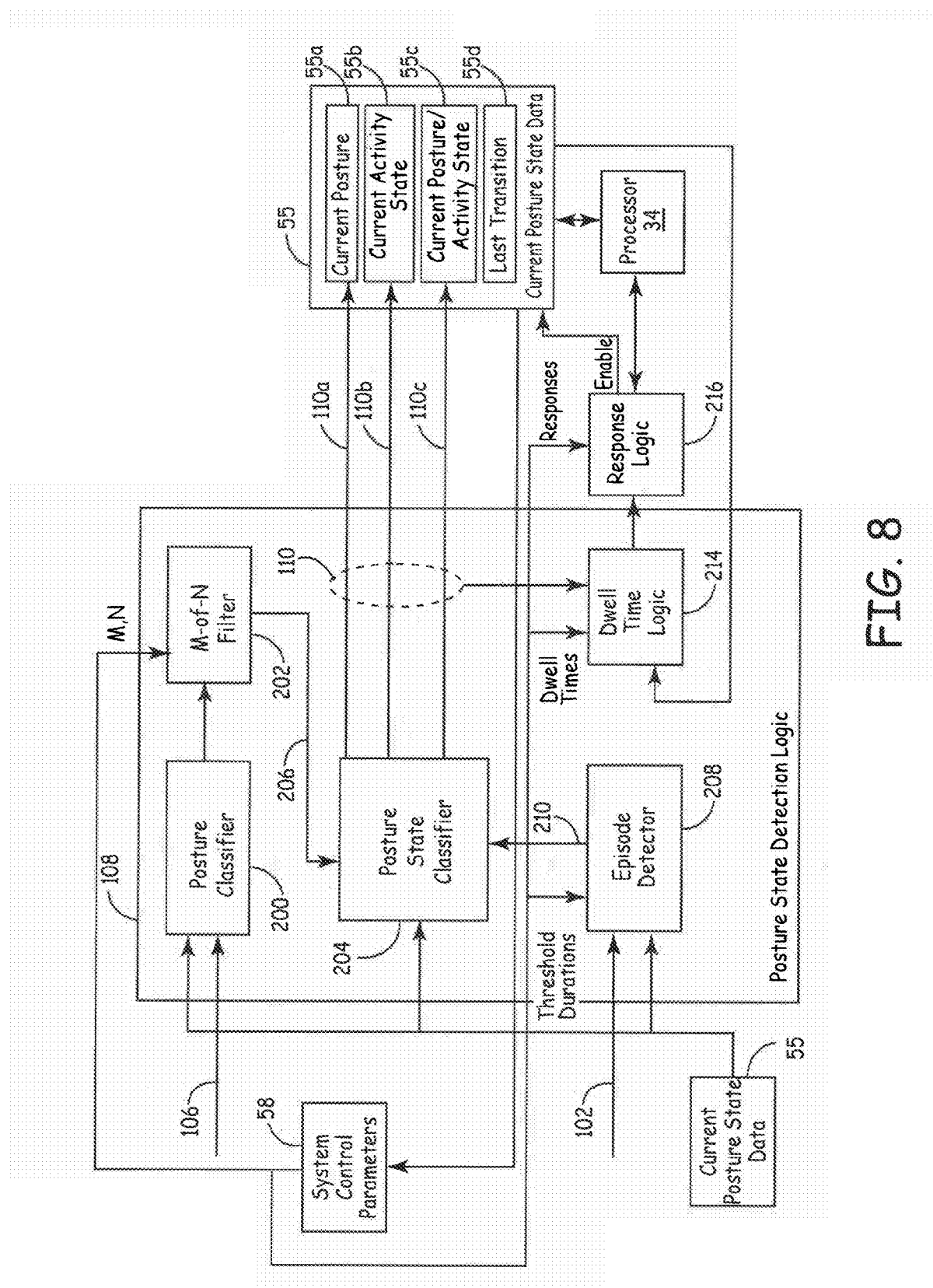
FIG. 8 is a functional block diagram of posture state detection logic.

FIG. 8 is a functional block diagram of posture state detection logic 108. Posture state detection logic 108 receives at least one activity signal on interface 102 from activity detection logic 100. For purposes of this discussion, it will be assumed this is an activity trend signal, act_trend, which is derived in the manner described in reference to FIG. 6. However, one or more other signals may be received from activity detection logic 100. In one embodiment, the signals that are received are selected using system control parameters 58 and/or current posture state data 55, as discussed above.

Posture state detection logic 108 further receives posture trend signals, pos_trendx, pos_trendy, and pos_trendz, on interface 106 from posture detection logic 104. The patient's posture state is classified based on the received signals, which are compared to the posture state definitions 52. In another embodiment, posture state detection logic 108 may receive only posture signals on interface 102 or only activity signals on interface 106 for use in classifying a patient's posture state, rather than both types of signals.

First, posture classification is considered. The signals received on interface 106 from posture detection logic 104 are provided to posture classifier 200. In the current example, these signals include pos_trendx, pos_trendy, and pos_trendz that are obtained for the x-, y- and z-axis signals, respectively. The three posture trend signals provide a vector in three-dimensional space. Posture classifier 200 compares this detected vector to each of the posture definitions 52a, which are a sub-set of posture state definitions 52. Recall that in one embodiment, each such posture definition 52a may include a defined posture vector and an associated tolerance that specifies a distance relationship with the defined posture vector. Posture classifier 200 determines whether the detected posture vector has the relationship with any of the posture vectors that is specified by the corresponding tolerance of a defined posture. Many mechanisms are available for making this determination, which is largely beyond the scope of this disclosure. Examples of the mechanisms used to make a determination as to whether the posture signals are associated with a defined posture are described in commonly-assigned patent applications entitled "Posture State Classification for a Medical Device" Ser. Nos. 12/433,004 and 12/432,993 referenced above.

If the signals provided on interface 106 have a specified relationship with a posture definition 52a, an indication of the defined posture for this definition is provided to M-of-N filter 202. For instance, a binary code indicative of the defined posture may be provided for this purpose. If no such match occurs, a code indicating the current posture is Unclassified may be provided to the M-of-N filter instead.

In one embodiment, M-of-N filter 200 utilizes a buffer that stores the indication for the most recently-detected posture and the preceding N-1 detected postures, for a total of N retained postures. If M of these N stored postures is a same posture, an indication of that "M-of-N posture" is provided by M-of-N filter 202 to posture state classifier 204 on interface 206. If M of the most recent N postures is not a same posture, M-of-N filter 202 will indicate on interface 206 that no valid M-of-N posture was detected.

As an example of the foregoing, assume that M-of-N filter 202 stores N of the most-recently-received posture codes in a buffer. Of these N most-recent posture codes, M of the codes are the same code that indicates the patient is in the Upright posture. The remaining codes indicate a mix of other postures. Since M of the posture codes are the same posture code (i.e., a code for the Upright posture), an indication of the Upright posture is provided on interface 206 to posture state classifier.

Next, assume that only M-1 of the codes were the same code indicating an Upright posture. The remaining ones of the N codes are varied, indicating a variety of postures. In this case, a signal indicating that no M-of-N posture was detected is provided to posture state classifier 204.

In one embodiment, the values of "M" and "N" may be selected by system control parameters 58 based on the current posture state data 55. For instance, when the current posture state is one associated with a higher level of activity, it may be desirable to increase the number of detected postures "N" that are taken into account by the M-of-N filter 202. Alternatively or additionally, it may be desirable to increase the number of postures "M" that are required to be detected for a particular posture before an indication of an M-of-N posture is provided to posture state classifier 204.

In yet another embodiment, the M-of-N filter 202 may operate based not only of the current posture state data, but on a potential posture state transition that may be about to, but has not yet, occurred. In this case, the value of "N" samples may be selected based on the current posture state data 55. However, the value of "M" may be selected based on which posture the patient may be about to enter. Such a determination may be made, for instance, by the posture indicated by the majority of N samples. Such values for "M" may be "hard-coded" or programmable, and may, but need not, be included as ones of system control parameters 58.

Next, activity state classification is considered. In this case, one or more signals are provided on interface 102 to episode detector 208. This logic operates in a way that may be similar to the M-of-N filter 202 that is described above in reference to posture detection. In particular, episode detector 208 determines whether this signal indicates an episode of a certain type of activity has been detected. If so, an indication of an activity state is provided to posture state classifier 204. If, however, the signal on interface 102 does not reflect an episode, an indication that no episode was detected is provided to posture state classifier 204.

In one embodiment, a determination as to whether an episode of activity occurred is based on whether a signal on interface 102 crosses a transition threshold and does not recross this threshold in an opposite direction for at least a predetermined period of time, referred to as the threshold duration. Both the transition threshold and the threshold duration may be specific to the current posture state data 55, and may further be specific to the direction in which the signal is trending.

The foregoing may be illustrated by considering the act_trend signal 147 provided by rolling mean logic 146 of FIG. 6 which describes a patient's overall activity level. This signal may be provided on interface 102 to episode detector 208. Assume this signal may have a value that ranges from 0 to 100, with "0" reflecting no activity, and 100 indicating a maximum level of activity. Further assume that activity state definitions 52b have been created called "Low" and "Moderate" to describe low and moderate levels of overall activity, respectively, based on the act_trend signal. The Low definition has been created for the range between 0-40, and the Moderate definition has been created for the signal range 40-80.

Without use of episode detector 208, as the act_trend signal trends upward, crossing the boundary of 40, the activity state classification would generally change from Low to Moderate according to the foregoing activity state definitions. If the act_trend signal then re-crosses this boundary in the downward direction, the activity state would again be re-classified to Low. Such re-classification may occur multiple times, especially if the act_trend signal hovers around the boundary for a period of time.

To prevent this oscillation, episode detector 208 may be employed. In one embodiment, episode detector 208 is used to impose a transition threshold at the boundary between two definition ranges. For instance, assume a transition threshold of "5" is selected for use with episode detector 208. In this case, the transition from Low to Moderate is moved upwards from 40 to 40+5, or 45. This forces the activity level to exceed the boundary between activity state definitions by some selected amount (in this case "5") before a transition is detected, and therefore prevents oscillation between two activity states if the patient is at an activity level that is substantially at the boundary.

If desired, this same transition threshold may be utilized when the act trend signal trends downward. In this case, it will be applied as a negative value. That is, the transition from Moderate to Low may be moved downwards from 40 to 5 less than 40, or 35.

This same transition threshold may be applied to other transitions associated with the act_trend signal 147. For instance, assume that a definition of High is created that is associated with a range of 80-100. As was the case described above, the transition from Moderate to High will not occur until the act trend signal reaches a value of 80+5, or 85. Similarly, the transition back to Moderate will not occur until the act trend signal reaches a value of 80±5, or 75.

If desired, two different transition thresholds may be utilized, one being associated with an upward signal trend, and a different transition threshold being associated with a downward trend. For instance, the transition threshold of 5 may be utilized when the act_trend signal is trending upward such that a switch from Moderate to High will not occur until a level of 86 is reached. However, a different transition threshold of 10 may be utilized, for instance, when the signal trends downward. In this case, the transition back to Moderate will not occur until the act_trend signal reaches 80–10, or 70. As was the case described above, use of two different transition thresholds in this manner prevents oscillation between two activity states if the patient is at an activity level that is substantially at a boundary.

In yet another embodiment, the transition threshold(s) may be specific to a particular transition. For instance, in an embodiment wherein the Low, Moderate, and High definitions are in use in the manner described above, each possible transition between defined activity levels (e.g., Low/Moderate, Moderate/Low, Moderate/High, High/Moderate, Low/High, High/Low) may be associated with a single unique transition threshold, or two unique transition thresholds (one for upward trends and another for downward trends).

In all of the foregoing embodiments, the transition thresholds that are in use at a given time may be selected based on current posture state data 55.

According to another aspect of the disclosure, transition durations may be utilized. A transition duration is the amount of time a signal level must remain above or below a transition threshold before a change in activity state will be detected. As an example, recall the foregoing example in which the transition threshold is 5 and the act_trend signal is transitioning from Moderate to High levels of activity such that a transition will not be detected until the signal is at 86 or higher. Further assume use of a transition duration of 10 seconds. This indicates the act trend signal must remain above 86 for at least 10 seconds before the activity state will change.

In one embodiment, a same transition duration may be selected for use with all transitions, regardless of whether the signal is trending upwards or downwards. In another embodiment, different transition durations may be used when the signal is trending upwards as compared to when it is trending downwards. In yet a different embodiment, the transition durations may be selected to be transition specific (e.g., Low/Moderate, Moderate/Low, Moderate/High, High/Moderate, Low/High, High/Low). In this latter case, the transition durations that are selected for a specific transition may be the same, or different, for upwards and downwards trends. That is, a first transition duration may be selected for an upward transition from Low to Moderate, and a different transition duration may be selected for a downward transition from Moderate to Low, and so on.

In any of the embodiments, the transition durations may be selected based on current posture state data 55. The transition durations may be used either alone, or in conjunction with, transition thresholds. Many possibilities are available. For instance, some, or all, of the transition thresholds may be set to 0 such that the boundaries appearing in the activity state definitions are used to determine an activity state transition. Alternatively or additionally, some, or all, of the transition durations may be set to 0 such that re-classification of activity state occurs as the value of an activity signal crosses the boundary that triggers the transition (either the definitional boundary or the transition threshold boundary).

It may be noted that a signal provided on interface 102 to episode detector 208 may not satisfy requirements of any of definitions 55. For instance, assume that definitions have only been created for Low and High levels of activity according to the associated ranges set forth above in the foregoing examples. The intermediate range of signal levels 41-80 has not been associated with any definition. Thus, if the act_trend signal trends upward out of the range for the Low activity classification, the signal will not favorably compare to any of the existing definitions. In this case, episode detector 208 may provide an indication on interface 210 to convey that no episode has been detected for the patient's activity state. This same no-episode signal may be used to identify the situation wherein the patient's activity state does falls within the boundaries of an activity state definition, but the transition threshold and/or transition duration have not been met such that an episode has not been detected.

In the foregoing manner, episode detector 208 provides a signal on interface 210 that is indicative of a patient's activity state. This signal is based on the posture state definitions 52 and the system control parameters 58, and indicates whether an activity episode has been detected, and if so, the activity state with which the episode is associated.

Posture state classifier 204 receives a signal on interface 210 from episode detector 208 that is based on activity state definitions 52b. Episode detector 208 further receives a signal on interface 206 from M-of-N filter 202 that that is based on posture definitions 52a. These signals are further compared to all other posture state definitions 52 to determine whether together the signals satisfy the requirements of any other posture state definitions.

As an example of the foregoing, the signal on interface 206 may be indicative of an Upright posture. The signal on interface 210 may be indicative of an episode of High activity. If one of posture state definitions 52 (e.g., Upright and Active posture state definition) has been created that is based on detection of both an Upright posture and a High activity state, an indication of this posture state is forwarded onto interface 110c. The current posture indication (i.e., Upright) and the current activity state indication (i.e., High) is also forwarded by posture state classifier 204 onto interfaces 110a and 110b, respectively.

In some cases, one or both of the posture and activity state signals on interfaces 206 and 210, respectively, may not identify a posture. For instance, if an M-of-N posture was not detected by M-of-N filter 202, the current posture is Unclassified, and this indication will be forwarded to interface 110a. Likewise, if an activity episode was not detected by episode detector 208, an indication of the Unclassified activity state is provided on interface 110b. In either of these cases, the posture state classification on interface 110c will likewise be Unclassified, since this signal takes into account both activity state and posture.

In another scenario, the posture and activity state indications on interfaces 206 and 210 may be associated with a defined posture and activity states, respectively, but there is no posture state definition that takes into account both of the posture indication and the activity state indication. For instance, there may be no posture state definition that has been created that takes into account an Upright posture and a High activity state classification. In one embodiment, in this scenario, the indication on interface 110c will likewise be "Unclassified", since no definition is available that takes into account both posture and activity state.

The information on interfaces 110a-110c may indicate three different posture states that may be exhibited by a patient at once, one associated with posture only (e.g., Upright) on interface 110a, one associated with activity state only (e.g., High) on interface 110b, and one associated with both posture and activity state (e.g., Upright and Active) on interface 110c. Alternatively, only one or two of interfaces 110a-110c may provide useful information, depending on the posture state definitions 52 in use, as discussed above. This information is all forwarded to dwell time logic 214.

Dwell time logic 214 may be used to insert a delay between the time a change in the patient's posture state has been detected on one of interfaces 110a-110c and the time this posture state change is used to initiate a particular type of response, such as a change in therapy. In this manner, dwell times are utilized to tailor the response times.

As a simple example, dwell time logic 214 has access to current posture state data 55 and thereby may determine the current posture 55a, current activity state 55b, and current posture/activity state 55c. Assume that dwell time logic 214 receives an indication of a posture on interface 110a that is different than current posture 55a. If a selectable dwell time $T_{Dwell}$ is in use within the system, dwell time logic 214 will allow this selected time period to elapse before dwell time logic 214 will provide an indication to response logic 216 to initiate a response for the posture change. Such a response may be change in therapy, for instance. Alternatively, the response may involve providing a notification, updating a log to record the new posture, storing some other information, initiating a communication session (as with an external or another internal device), or some other action.

In a similar manner, dwell time logic 214 may impose a dwell time for the activity state indication provided on interface 110b. This may be the same, or a different, dwell time from that which is used when a change in posture is detected. Likewise, a same or different dwell time may be imposed when a particular change in the posture/activity state indication provided on interface 110c. A dwell time may also be imposed based on a transition involving a posture, activity state, or the posture/activity state.

In all of the cases discussed above, the dwell time that is being used by dwell time logic 214 may be selected based on current posture state data 55.

In one embodiment, the dwell time may alternatively or additionally be response-specific. Thus, after a particular signal combination appears on interface 110, a first dwell time may be imposed before initiation of a first response (e.g., change in therapy delivery), a second dwell time may be imposed before initiation of a second response (e.g., an event notification) and so on. This provides flexibility in how responses are generated in response to detection of particular posture state data.

In one embodiment, the data on interface 110 is used to update current posture data 55, as shown in FIG. 8. That is, the current posture 55a may be updated based on the newly-detected posture provided on interface 110a, the current activity state 55b may be updated based on the newly-detected activity state on interface 110b, and current posture/activity state 55c that involves both posture and activity may be updated based on the newly-detected posture state on interface 110c.

In one embodiment, updating of current posture data 55 may occur whenever any of the signals on interface 110 provides something other than an Unclassified indication that is different from that stored within current posture state data 55. Thus, if the posture on interface 110a is Upright and the other two indications are Unclassified, and current posture 55a is Lying Down, updating will be enabled. The new current posture state data 55 will reflect the Upright posture, the Unclassified activity state, and the Unclassified current posture/activity state.

Updating of current posture data 55 may be performed under control of processor 34, and/or under control of other logic. In one embodiment, the updating will occur after a predetermined dwell time has elapsed as determined by dwell time logic 214. This dwell time may be a specific time period that is imposed prior to updating of current posture state data 55, or may be a general dwell time that is used to trigger other types of responses. In this way, one of the actions controlled by response logic 216 and dwell time logic 214 may be the updating of current posture state data 55.

As noted above, a dwell time that is being used by dwell time logic 214 may be selected by system control parameters 58 based on current posture state data 55. For instance, consider the case wherein the patient was Lying Down as indicated by current posture 55a. The new posture indication of "Upright" is provided on interface 110a. It may be known that a change in therapy in response to this type of transition should be initiated only after it is known that the patient is well established in the Upright posture. Therefore, it may be desirable to allow a longer dwell time to elapse between the time the transition is detected and the time therapy delivery is initiated. In other cases, such as notifications, it may be more desirable to reduce the dwell time to 0 so that a notification is issued immediately when a posture transition is indicated on interface 110a.

When dwell times are used, posture states that are assumed for shorter than the corresponding dwell time will not prompt an associated response. Moreover, in an embodiment that utilizes dwell times to update current posture state data 55, posture states that are assumed for shorter than a corresponding dwell time will not be stored in current posture state data 55, and will not be used to control signal processing.

In one embodiment, dwell time logic 214 may utilize one or more software or hardware timers that are re-started each time current posture state signals on interface 110 are updated. The timer will maintain a measure of the time elapsed since the posture state change. This measure may be compared to a dwell time, which may be selected based on the signals on interface 110, the current posture state data 55, and/or the type of response to be initiated. The response is not initiated until the elapsed time, as measured by the timer, equals or exceeds the dwell time that is needed to initiate the response.

In one embodiment, response logic 216 may be provided to receive a signal from dwell time logic 214 and cause some action, or response to be generated. This response may be a therapy modification that is controlled by processor 34 and/or delivered by therapy module 32. This response may be a notification, such as a communication delivered by telemetry logic 38 to an external device such as programmer 20. A response may involve updating current posture state data 55 and/or updating posture history file 54. Other responses are possible within the scope of the current invention. In one embodiment, the responses that may be available at a given time may be based on current posture state data 55.

It is appreciated that FIG. 8 is a functional block diagram. Any of the logic blocks shown in FIG. 8 may be implemented in hardware, programmed instructions, or some combination thereof. Moreover, the interfaces between logic blocks may be implemented in many ways. For instance, one or more of the logic blocks of FIG. 8 need not be physically connected to adjoining logic blocks, but may instead be logically connected, as by processor 34 transferring information from one logic block to another, for instance.

The exemplary embodiment of FIG. 8 illustrates system control parameters 58 providing information to ones of the logic blocks to control operation. However, as was described above, this control may instead by exercised directly by current posture state data 55. That is, an indication of a current posture state may be provided to one or more of the various logic blocks for use in selecting an operation mode. As a specific example, such an indication may be provided to M-of-N filter 202 for use in selecting an operating mode that determines at least one of M and N.

The examples described in reference to FIG. 8 describe a posture signal and an activity state signal that are provided to posture state detection logic 108. The activity state signal is an overall activity level. However, this is merely for exemplary purposes, and one or more signals indicative of motion may be used instead, such as a vector indication of velocity of motion or a vector indicative of acceleration of motion. These vectors, like the posture vectors, may be compared to vectors referenced in posture state definitions for use in classifying a posture state according to any of the mechanisms and techniques described herein.

It may be appreciated that some logic blocks of FIG. 8 may be omitted or used for other purposes, without changing the scope of the invention. For instance, episode detector 208 may be readily adapted for use in classifying a posture change episode, instead of, or in addition to, being employed to classify an activity episode. Similarly, M-of-N filter 202 may be adapted for use in classifying an activity state change, instead of, or in addition to, being employed to detect an M-of-N posture.

It may further be appreciated that the data stored by current posture state data 55 is merely exemplary, and more or fewer data items may be stored in other embodiments. For instance, in a simplified version, only current posture 55a and/or current activity state 55b need be stored. In yet another variation, current posture 55a and/or activity state 55b may be reported using a single encoded or master-bitted value. For instance, such a value may be provided by posture state classifier 204 to current posture state data 55. Such a value may provide all information currently shown stored as current posture 55a, current activity state 55b, and current posture/activity state 55.

Thus, it will be understood that the logic blocks shown in FIGS. 6-8 are largely exemplary. Those skilled in the art may contemplate other processing steps for use in obtaining activity and posture signals. For instance, other mechanisms of combining signals (e.g., summation, subtraction, etc.) may be contemplated. According to the current disclosure, it may be advantageous to control such processing steps based on the current posture state data 55 and system control parameters 58.

Figure 9:
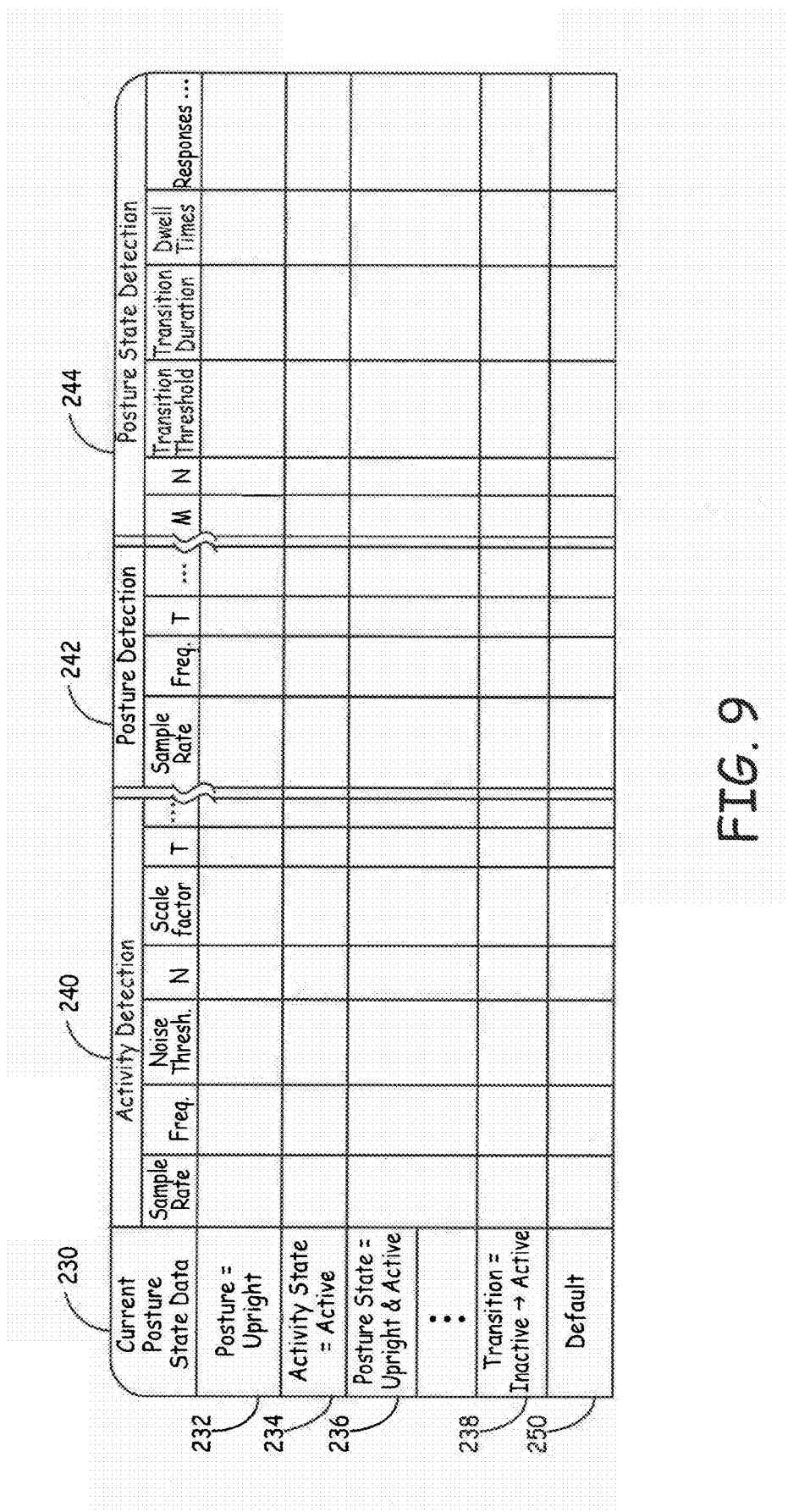
FIG. 9 is a data structure illustrating one mechanism for managing and using system control parameters according to the current disclosure.

FIG. 9 is a data structure illustrating one mechanism for managing and using system control parameters 58 according to the current disclosure. Each row ("entry") in this data structure is associated with either a posture state or a transition associated with a posture state, as shown in column 230. The posture state may be expressed in terms of posture only, activity state only, or both. As a specific example, row 232 is associated with an Upright posture, row 234 is associated with an activity state of Active, and row 236 is associated with an Upright & Active posture state that is based both on posture and activity. Row 238 involves a posture state transition from an Inactive posture state to an Active posture state.

Any number of such entries indicative of different posture states and posture state transitions may be included in a data structure of the type shown in FIG. 9. The number of entries may be based on how precisely the system control parameters are to be controlled, and on the number of posture state definitions in use in the system at a given time.

The data structure of FIG. 9 stores values for system control parameters to use when a corresponding posture state or transition is detected. For instance, columns 240 provide system control parameter values associated with processing sensor signals for activity detection. Such system control parameter values were discussed in association with FIG. 6, and may include, for example, sampling rate, filter control parameters (e.g., frequency selection), noise threshold, the value N for determining an activity count, a scale factor, a time period T used to determine a rolling mean, and so on. This list is not intended to be exhaustive, and may include any or all of the values discussed above in reference to FIG. 6, and may additionally or alternatively include other system control parameters needed to perform other types of processing not discussed in the example of FIG. 6.

Similarly, data structure of FIG. 9 may additionally or alternatively include columns 242 that relate to posture detection, and may include those system control parameters discussed in association with FIG. 7, such as sampling rate, filter control (e.g., frequency selection), a time period T used to determine a rolling mean (which may be different than that used to determine rolling mean for activity detection), and so on. This list is not intended to be exhaustive, and may include any or all of the values discussed above in regards to FIG. 7, and may additionally or alternatively include other system control parameters needed to perform other types of processing not discussed in the example of FIG. 6.

The exemplary data structure of FIG. 9 may additionally or alternatively include columns 244 that relate to posture state detection and that control how posture classification, activity classification, and other posture state classification occurs. Such parameter values may include values discussed in regards to FIG. 8, including but not limited to, "M" and "N" used by an M-of-N filter, a transition threshold and duration employed for episode detection, dwell times, types of responses that are available for a given type of posture state data, and so on.

The data structure shown in FIG. 9 may be used to select a set of system control parameter values for use at a given moment in time. For instance, after current posture state data 55 has been updated, the newly-stored information may be compared to data stored in column 230 to locate a matching entry. When such a match occurs, values stored within one or more of the other columns 240-244 of the data structure may subsequently be used to control how processing of signals of sensor 40 will occur.

The way the parameter values are used will vary based on the embodiment. In one example, one or more of the values may be retrieved from the data structure of FIG. 9 (e.g., by a processor) and loaded into storage devices associated with various ones of the logic blocks of FIGS. 5-8 for use in exercising control over signal processing hardware and/or software. Alternatively or additionally, a processor (e.g., processor 34) may retrieve one or more of the system control parameter values from the applicable entry of the data structure of FIG. 9 for use in controlling how software will be executed to accomplish a logical function associated with one or more of the logic blocks of FIGS. 5-8. In yet another embodiment, one or more of the system control parameter values may be provided via one or more interfaces that physically couple storage devices storing the parameter(s) to the logic blocks. Thus, the manner in which this control is exercised may vary depending on how the functional blocks are implemented.

Returning to the posture states and transitions shown in FIG. 9, it may be appreciated that a patient may be in multiple posture states at once. For instance, at the same time the patient is in an Upright and Active posture state (as associated with row 236) per current posture/activity state 55c, the patient may also be classified in the Upright posture state (associated with row 232) that is based only on the patient's upright position per current posture 55a. The patient may at the same time be in the Active posture state (associated with row 234) that is based only on the patient's activity level per current activity state 55b. At the same time, the current posture state data 55 may reflect that the last transition that occurred was from the Inactive to the Active activity state (associated with row 238). Thus, in one embodiment, the search of a data structure such as that shown in FIG. 9 could potentially identify multiple entries that may be associated with the patient's current posture state data 55. If these entries contain different system control parameter values, selection must be performed to determine which set of parameter values should be used in this instance.

To address the above-described situation, the entries may be ordered within the data structure in a priority order. For instance, if the current posture 55a is to be the deciding factor in the system control parameters that are being used at a given time, all of the posture states that are based on just posture may be ordered as the first rows in the data structure. For instance, this would include row 232, which is shown positioned first in the data structure of FIG. 9. Conversely, if the current posture/activity state 55c is to control which parameter values are used, the posture states that are determined based on both posture and activity state may be positioned to appear in the first rows of the table, and so on. As a result, if the table is searched in row order, the first matching entry may be used to determine the values for the system control parameters.

In another embodiment, some other mechanism may be used to prioritize multiple entries that could be potentially matched to the same current posture state data 55 at a given time, but that store different system control parameter sets. For instance, a priority field may be included in each entry to identify the relative importance to be assigned to the entry as compared to other potentially related entries. Alternatively, some other linking field may be created to link related entries in an ordered manner that identifies relative priority. Other mechanisms are possible for determining which of multiple the posture states/transitions should be given priority.

In some circumstance, the data stored by current posture state data 55 may not locate a matching entry in the data structure. According to one aspect, if desired, one or more default entries may be provided at the end of the data structure, such as shown in row 250. The system control parameter values included in this entry may be used in such cases wherein none of the entries match the current posture state data 55. Alternatively, in the event no match is found, the system control parameter values may be left unchanged until new posture state data is available that will result in a match.

It may be desirable to include as one of the default entries system control parameters to be employed when the system is first initialized and employed with a given patient. Such default system control parameter values may be employed, for instance, when the posture state definitions 52 are being created using patient participation, if such a mechanism is employed in the embodiment.

The types of system control parameters and/or the posture state definitions 52 to be reflected in a data structure such as that of FIG. 9 may be pre-determined by a device manufacturer and pre-loaded into the system. Alternatively, some or all of the parameters, parameter values, and definitions may be defined by a clinician or other user. If desired, the parameter values included in a data structure such as shown in FIG. 9 may be selected on a patient-by-patient basis by a user. Such a selection process may involve prompting a user to assume a posture and/or an activity state, and creating a posture state definition for the assumed activity, which may be stored as one of the posture state definitions 52. An entry may then be created in a data structure such as shown in FIG. 9 that is linked to, or otherwise identifies, this posture state definition. The optimal signal processing values to be used to process the signal may be determined (e.g., by adjusting parameters to determine which provides optimal results). The determined values may be entered in the appropriate entry of the data structure of FIG. 9. Of course, other ways for selecting the values on a patient-by-patient basis are available within the scope of the disclosure.

Figure 10:
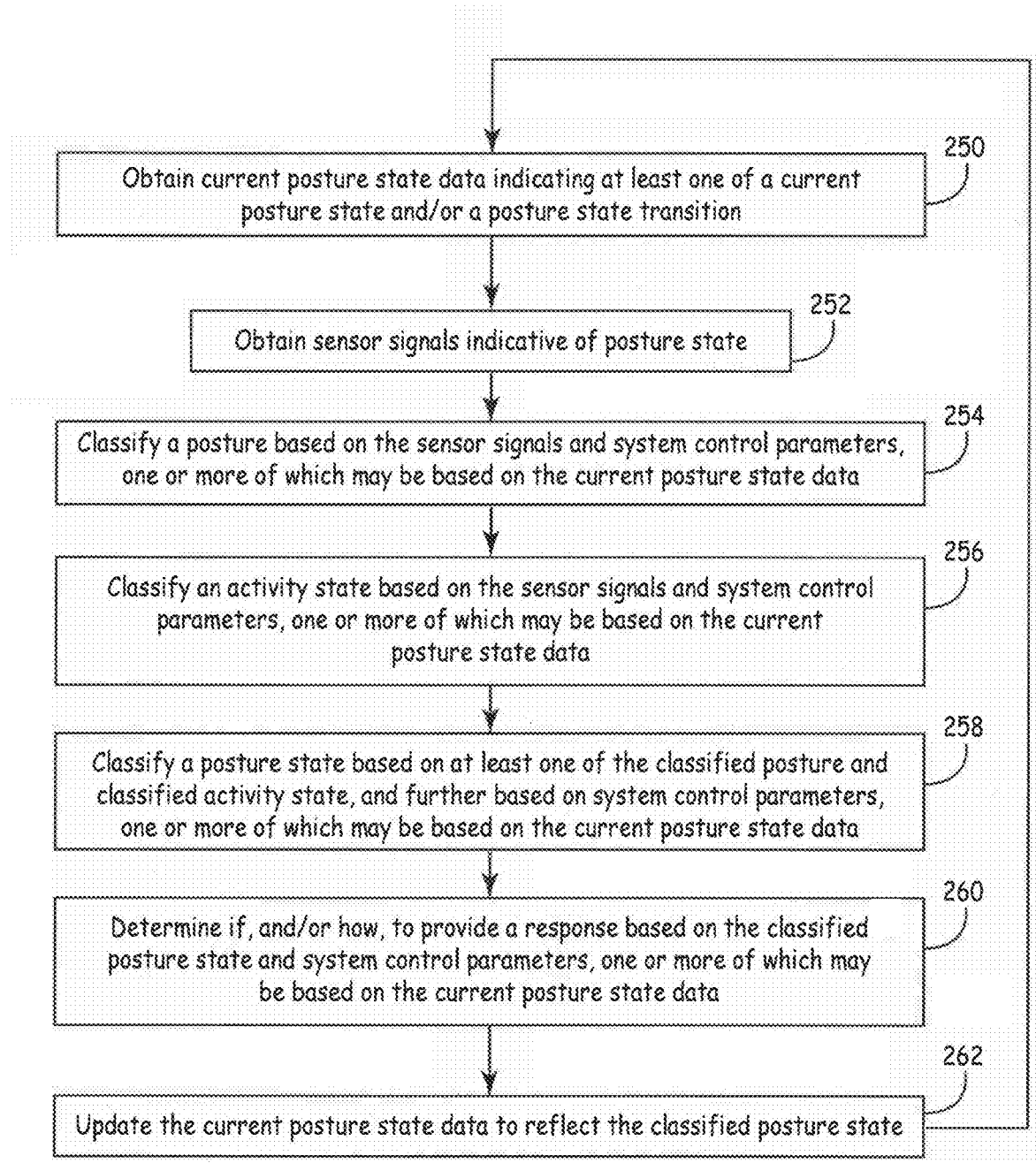
FIG. 10 is a flow diagram of one method according to the current disclosure.

FIG. 10 is a flow diagram of one method according to the current disclosure. Current posture state data is obtained that indicates at least one of a current posture state and/or a posture state transition (250). The current posture state may be associated with a posture, an activity state, or both. Similarly, the posture state transition may be associated with a most recent posture transition, a most recent activity state transition, or both.

Sensor signals may be obtained that are indicative of a patient's posture state associated with at least one of posture and activity state (252). The patient's posture may be classified based on the sensor signals and system control parameters, wherein one or more of the system control parameters may be based on the current posture state data (254).

The patient's activity state may be classified based on the sensor signals and system control parameters, wherein one or more of the system control parameters may be based on the current posture state data (256). A posture state may be classified for the patient based on at least one of the classified posture and the classified activity state, and the system control parameters, wherein one or more of the system control parameters may be based on the current posture state data (258).

It may further be determined if, and/or how, to provide a response based on the classified posture state and system control parameters, one or more of which may be based on the current posture state data (260). For instance, the type of responses available at a given time may be based on the patient's current posture state data. In some cases, there may be no responses that are to be initiated when the current posture state data stores a certain data set. For other posture state data, one or more responses may be initiated. Such responses may include the initiation of therapy delivery, the modification of therapy delivery, the storing of data, the prompting of a communication session with an external device, the delivery of a notification, the initiation of certain physiological measurements (e.g., the initiation of a heart rate measurement, etc.), or any other type of action that may be initiated or performed by a medical device.

The way the responses are initiated may also be selected based on the patient's current posture state data. For instance, the timing associated with therapy delivery may be affected by dwell times which are selected based on current posture state data.

Finally, the posture state data may be updated to reflect the classified posture state (262). In one embodiment, this may involve updating the current posture 55a, the current activity state 55b, the current posture/activity state 55c, and/or the last transition 55d, or some subset thereof. As discussed above, values for some or all of these data items may be encoded or otherwise represented by a single value, thereby compressing the data.

The process of FIG. 10 may then be repeated by returning to step 252 to obtain additional sensor signals and use the new current posture data to classify the patient's posture state.

It may be appreciated that the method of FIG. 10 may be modified in many ways within the scope of the current disclosure. For instance, in one embodiment, only a subset of steps 254-260 are performed based on the current posture state data, with the remaining steps being performed using predetermined system control parameters. In another embodiment, it may be desirable to eliminate some of steps 254-260 altogether. Thus, the method of FIG. 10 is exemplary only, and not limiting.

Those skilled in the art will recognize that various modifications may be made to the systems, methods, and techniques described herein. For instance, the methods described by the various flow diagrams may be implemented by a processor such as processor 34 that is executing programmed instructions stored as programs 50. Alternatively, some of the steps of the methods may be implemented in hardware such as control logic 41. In many cases, steps may be re-ordered, and some steps may be eliminated. Thus, the description of the embodiments discussed above is merely exemplary, with the scope of the invention to be defined by the Claims that follow.

What is claimed is:

1. A medical device system, comprising:
a storage device configured to store current posture state data describing a posture state in which a patient has previously been classified;
a sensor configured to sense one or more signals indicative of at least one of a posture and an activity state of the patient; and
control logic configured to process the one or more signals in a selectable manner that is based on the current posture state data, and after processing of the one or more signals in the selectable manner, to utilize the processed one or more signals to classify a patient as being in a posture state, wherein the posture state in which the patient has previously been classified is a posture state in which the patient was most recently classified.

2. The system of claim 1, wherein the sensor is a three-axis accelerometer.

3. The system of claim 1, wherein the sensed one or more signals are sampled at a sampling rate selected based on the current posture state data.

4. The system of claim 1, wherein the sensed one or more signals are filtered to retain selected frequencies that are selected based on the current posture state data.

5. The system of claim 1, wherein the control logic includes an M-of-N filter to identify a posture state indicated by M of N sampled posture states, and wherein at least one of M and N is selected based on the current posture state data.

6. The system of claim 1, wherein the control logic includes an episode detector to determine whether a processed one of the one or more signals crosses a signal level identified by a transition threshold and does not re-cross the transition threshold for at least a time period identified by a transition duration, wherein at least one of transition threshold and transition duration are selected based on the current posture state data.

7. The system of claim 1, further including response logic configured to initiate a response based on the posture state indicated by the processed one or more signals.

8. The system of claim 7, wherein the response is further based on the current posture state data.

9. The system of claim 7, wherein the control logic includes dwell time logic configured to impose a dwell time before the response logic initiates the response.

10. The system of claim 9, wherein the dwell time is selected based on the current posture state data.

11. The system of claim 7, wherein the response involves a therapy delivered to the patient.

12. The system of claim 1, wherein the control logic updates the current posture state data to indicate the posture state indicated by the processed one or more signals.

13. The system of claim 1, wherein the control logic processes the one or more signals to derive a vector indicative of at least one of posture and activity state.

14. The system of claim 1, wherein the control logic processes the one or more signals to derive an activity level indicative of activity state.

15. A method, comprising:
receiving a signal from a sensor that indicates a posture state of a patient;
obtaining current posture state data identifying a posture state in which the patient was most recently classified;
processing the received signal in a manner that is based on the current posture state data and thereafter, utilizing the processed signals to determine at least one of an activity state and a posture of the patient; and
initiating, by a medical device, a response based on the classification of the processed signal.

16. The method of claim 15, further including updating the current posture state data to describe the classification of the processed signals.

17. The method of claim 15, wherein initiating the response includes delivering therapy to the patient based on the classification of the processed signals.

18. The method of claim 15, further including sampling the signal from the sensor at a rate based on the current posture state data.

19. The method of claim 15, wherein the current posture state data identifies a transition associate with the posture state in which the patient was most recently classified, and wherein processing of the received signals is performed in a manner that is based on the transition.

20. A method, comprising:
receiving a signal from a sensor that indicates a posture state of a patient;
obtaining from a storage device current posture state data identifying a posture state in which the patient was most recently classified;
processing the received signal based on the current posture state data to determine an activity state of the patient; and
updating the current posture state data based on the determined activity state of the patient.

21. The method of claim 20, further including:
processing the received signal based on the current posture state data to determine a posture of the patient; and
updating the current posture state data based on the determined posture of the patient.

22. The method of claim 21, wherein at least one of determining the activity state of the patient and determining the posture of the patient is performed based on a sampling rate selected based on the current posture state data.

23. The method of claim 21, wherein at least one of determining the activity state of the patient and determining the posture of the patient comprises filtering the received signal in a manner selected based on the current posture state data.

24. The method of claim 20, further comprising delivering therapy to the patient based on the determined activity state of the patient.

25. The method of claim 24, further comprising delivering therapy to the patient via an implantable therapy delivery device.

26. The method of claim 21, wherein at least one of determining the activity state of the patient and determining the posture of the patient comprises obtaining a sum of N successive samples of the received signal, wherein N is selected based on the current posture state data.

27. A non-transitory storage medium for storing instructions executed to cause a processor to perform a method, comprising:
receiving signals indicating a posture of a patient;
retrieving current posture state data indicating a posture state in which the patient was most recently classified;
processing the received signals in a manner controlled by the current posture state data; and
determining from the processed signals a classification of the posture of the patient.

28. The storage medium of claim 27, wherein the method further comprises:
receiving signals indicating an activity state of the patient;
processing the received signals indicating the activity state in a manner controlled by the current posture state data; and determining a classification of the activity state of the patient.

29. The storage medium of claim 27, wherein the method further comprises controlling delivery of therapy to the patient based on the classification of the posture.

30. The storage medium of claim 27, wherein the signals indicating a posture of the patient are also indicative of activity.

31. The medical device system of claim 1 further comprising a programming device, and wherein the programming device comprises the control logic.

32. The medical device system of claim 1 further comprising an implantable medical device, and wherein the implantable medical device comprises the control logic.

33. A method, comprising:
sensing a signal indicative of a posture state of a patient;
processing, by control logic of a medical system, the sensed signal in a manner that is based on a posture state in which the patient was previously classified by the control logic; and
classifying the posture state of the patient based on processing of the sensed signal.

34. A medical system, comprising:
a sensor configured to sense a signal indicative of a posture state of a patient; and
control logic configured to process the signal in a manner that is based on a posture state in which the patient was previously classified by the control logic and to classify, based on the processed signal, a posture state of the patient.

35. The medical system of claim 34, wherein the control logic resides within an implantable medical device.

36. The medical system of claim 34, wherein the control logic resides within a programming device.

37. The medical system of claim 34, wherein the signal is sampled at a rate selected based on the posture state in which the patient was previously classified by the control logic.

38. The medical system of claim 34, wherein the signal is filtered in a manner selected based on the posture state in which the patient was previously classified by the control logic.

39. The medical system of claim 34, wherein therapy is delivered to the patient based on the posture state of the patient.

40. The method of claim 33, further comprising delivering therapy to the patient based on the classified posture state of the patient.

41. The method of claim 40 further comprising delivering therapy to the patient via an implantable medical device.

42. The method of claim 33, wherein processing, by control logic of a medical system, the sensed signal in a manner that is based on a posture state in which the patient was previously classified comprises selecting at least one of a sampling rate and a number of samples of the sensed signal for use in classifying the posture state.

43. The method of claim 33, further comprising initiating a response based on classifying a posture state of the patient after the patient has occupied the posture state for a predetermined dwell time.

44. The method of claim 43, wherein the predetermined dwell time is selected based on the posture state in which the patient was previously classified by the control logic.

* * * * *